(12) United States Patent
Gupta et al.

(10) Patent No.: US 10,420,723 B2
(45) Date of Patent: Sep. 24, 2019

(54) MILK-DERIVED MICROVESICLE COMPOSITIONS AND RELATED METHODS

(71) Applicant: University of Louisville Research Foundation, Inc., Louisville, KY (US)

(72) Inventors: Ramesh C. Gupta, Prospect, KY (US); Radha Munagala, Louisville, KY (US); Farrukh Aqil, Louisville, KY (US); Jeyaprakash Jeyabalan, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 15/910,322

(22) Filed: Mar. 2, 2018

(65) Prior Publication Data
US 2018/0185285 A1  Jul. 5, 2018

Related U.S. Application Data

(63) Continuation of application No. 14/770,634, filed as application No. PCT/US2014/018601 on Feb. 26, 2014, now Pat. No. 9,943,482.

(60) Provisional application No. 61/769,551, filed on Feb. 26, 2013.

(51) Int. Cl.
| | |
|---|---|
| C07H 21/02 | (2006.01) |
| C07H 21/04 | (2006.01) |
| A61K 9/127 | (2006.01) |
| A61K 31/704 | (2006.01) |
| A61K 31/7042 | (2006.01) |
| A61K 9/00 | (2006.01) |
| A61K 9/51 | (2006.01) |
| A61K 31/12 | (2006.01) |
| A61K 31/337 | (2006.01) |
| A61K 31/343 | (2006.01) |
| A61K 31/352 | (2006.01) |
| A61K 31/585 | (2006.01) |
| A61K 31/7048 | (2006.01) |
| A61K 31/7105 | (2006.01) |

(52) U.S. Cl.
CPC .......... *A61K 9/1276* (2013.01); *A61K 9/0019* (2013.01); *A61K 9/0043* (2013.01); *A61K 9/0053* (2013.01); *A61K 9/5176* (2013.01); *A61K 31/12* (2013.01); *A61K 31/337* (2013.01); *A61K 31/343* (2013.01); *A61K 31/352* (2013.01); *A61K 31/585* (2013.01); *A61K 31/704* (2013.01); *A61K 31/7042* (2013.01); *A61K 31/7048* (2013.01); *A61K 31/7105* (2013.01)

(58) Field of Classification Search
CPC .......................... C12N 15/113; C12N 2310/11
See application file for complete search history.

(56) References Cited

U.S. PATENT DOCUMENTS

2012/0315324 A1* 12/2012 Zhang .................. A61K 31/713

OTHER PUBLICATIONS

Hata et al. (Biochemical and Biophysical Research Communications, 2010, vol. 396, pp. 528-533).*

* cited by examiner

*Primary Examiner* — Amy H Bowman
(74) *Attorney, Agent, or Firm* — Law Office of J.L. Simunic; Joan Simunic

(57) ABSTRACT

A composition is provided that comprises a therapeutic agent encapsulated by a milk-derived microvesicle. The compositions can include therapeutic agents such as phytochemical agents or chemotherapeutic agents, while the milk-derived microvesicle can be derived from raw milk or colostrum. Further provided are methods for isolating a microvesicle that includes the steps of obtaining an amount of milk, and subjecting the milk to a series of sequential centrifugations configured to yield greater than about 300 mg of microvesicle protein per 100 ml of milk. Methods of modifying an immune response and treating a cancer in which a milk-derived microvesicle composition is administered are also provided.

19 Claims, 25 Drawing Sheets

E1α = Enolase 1α; FAS = Fatty acid synthase; MFG-E8 = Milk fat globulin-EGF factor 8;
MHC II = Major histocompatibility complex class II; PIGR = poly Ig receptor; XDH = Xanthine dehydrogenase.

MILK-DERIVED MICROVESICLE COMPOSITIONS AND RELATED METHODS

RELATED APPLICATIONS

This application claims priority from U.S. Non-Provisional application Ser. No. 14/770,634, filed Aug. 26, 2015, and U.S. Provisional Application Ser. No. 61/769,551, filed Feb. 26, 2013, the entire disclosures of which are incorporated herein by this reference.

GOVERNMENT INTEREST

This invention was made with government support under grant numbers CA-118114 and CA-125152 awarded by the National Institutes of Health. The government has certain rights in the invention.

TECHNICAL FIELD

The presently-disclosed subject matter relates to milk-derived microvesicle compositions and methods of isolating and using the same for the treatment of disease. In particular, the presently-disclosed subject matter relates to compositions that comprise therapeutic agents encapsulated by milk-derived microvesicles and that are useful in the treatment of disease.

BACKGROUND

Oral delivery of many compounds, natural or synthetic, generally results in limited bioavailability, and thus often requires large doses of the compounds in order to achieve efficacy. Bolus doses of many such compounds though are not feasible in humans due to toxicity concerns or due to the unavailability of compounds. Furthermore, some natural compounds, despite being administered in large doses (e.g., curcumin), have still resulted in limited bioavailability in pre-clinical and clinical studies due to poor absorption and rapid hepatic metabolism. On the other hand, chemotherapeutic agents often elicit dose spikes and are highly toxic with severe short-term and long-term side effects. As such, compositions and methods that decrease dose-related toxicities while maintaining drug efficacy are considered to be of great importance.

In this regard, numerous laboratories have attempted to embed or attach certain agents in liposomes, polymer-based formulations, or nanoparticles to improve oral bioavailability. Nevertheless, while these approaches have resulted in some improvements in bioavailability, the carriers themselves, particularly polymer-based nanoparticles, can have toxicity if not cleared effectively. Scalable production of polymer-based and other nanoparticles also continues to be a limitation. Recently, natural nanoparticles, such as exosomes having a size in the range of 30 to 100 nm size, have shown the potential to circumvent problems associated with traditional nanoparticles. However, the ability to effectively encapsulate a specific therapeutic agent or an effective amount of a therapeutic agent in natural nanoparticles, such as an exosomes, has proven difficult in many instances. Additionally, current approaches of isolating exosomes from various body fluids, including milk, are based on differential centrifugation, sucrose-density gradient, Sephadex chromatography, polymer-based (e.g., ExoQuick), and many others. To date though, there are no procedures to isolate natural nanoparticles, such as exosomes or other microvesicles, rapidly and in the bulk quantities required for treating a disease on a commercial level.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes milk-derived microvesicle compositions and methods of isolating and using the same for the treatment of disease. In particular, the presently-disclosed subject matter includes compositions that comprise therapeutic agents, including both hydrophilic and lipophilic therapeutic agents, that are encapsulated by milk-derived microvesicles and that are useful in the treatment of disease.

In some embodiments of the presently-disclosed subject matter, a composition is provided that comprises an effective amount of a therapeutic agent encapsulated by a milk-derived microvesicle. In some embodiments, the milk-derived microvesicle is a colostrum-derived microvesicle. In some embodiments, the milk-derived microvesicles form part of a pharmaceutical composition, where the milk-derived microvesicles are combined with a pharmaceutically-acceptable vehicle, carrier, or excipient.

With regard to the therapeutic agents that are encapsulated within a milk-derived microvesicle of the presently-disclosed subject matter, in some embodiments, the therapeutic agent is selected from the group consisting of a phytochemical agent and a chemotherapeutic agent. For example, in some embodiments, the therapeutic agent is a phytochemical agent, such as curcumin, demethoxycurcumin, delphinidin, cyanidin, withaferin A, tanshinone, bilberry anthocyanidins, or combinations thereof. In some embodiments, the therapeutic agent is a bilberry anthocyanidin mixture, punicalagin, or tanshinone. As another example, in other embodiments, the therapeutic agent is a chemotherapeutic agent, such as doxorubicin, paclitaxel, docetaxel, or combinations thereof. In further embodiments, the milk-derived microvesicles comprising one or more miRNA molecules, such as, in certain embodiments, miR-155 and miR-223.

Further provided, in some embodiments of the presently-disclosed subject matter, are methods for isolating a microvesicle. In some embodiments, a method for isolating a microvesicle is provided that comprises the steps of: obtaining an amount of milk; and subjecting the milk to a series of sequential centrifugations that are configured to yield greater than about 50 mg (e.g., greater than about 300 mg) of microvesicle protein per 100 ml of milk. For instance, in some embodiments, the series of sequential centrifugations comprises a first centrifugation at 20,000×g at 4° C. for 30 min, a second centrifugation at 100,000×g at 4° C. for 60 min, and a third centrifugation at 120,000×g at 4° C. for 90 min. In some embodiments, the milk is raw milk and, in some embodiments, the milk is colostrum. In some embodiments, upon isolation, the isolated milk-derived microvesicles can then be stored at a concentration of about 5 mg/ml to about 10 mg/ml.

Still further provided, in some embodiments of the presently-disclosed subject matter, are therapeutic methods wherein the milk-derived microvesicles described herein are administered orally, intravenously, intranasally, or intraperitoneally to treat a disease or disorder in a subject. As one example of a therapeutic method, in some embodiments, a method of modifying an immune response is provided that comprises administering to a subject in need thereof an effective amount of a composition that includes a therapeutic agent encapsulated by a milk-derived microvesicle. In some embodiments of such methods, administering the composition reduces an amount of an inflammatory cytokine in a subject including, in certain embodiments, a reduction in the amount of tumor necrosis factor-α, interleukin-1β, interferon γ, and/or interleukin-6. In some embodiments, administering the composition reduces an amount of NF-κB signaling in a subject.

In other embodiments of the therapeutic methods, a method of treating a cancer in a subject is provided that comprises administering to a subject in need thereof an effective amount of a composition including a therapeutic agent encapsulated by a milk-derived microvesicle. In some embodiments, the cancer is selected from the group consisting of breast cancer, uterine cancer, lung cancer, prostate cancer, ovarian cancer, cervical cancer, and pancreatic cancer. In some embodiments, the therapeutic agent is selected from the group consisting of a phytochemical agent and a chemotherapeutic agent.

Further features and advantages of the present invention will become evident to those of ordinary skill in the art after a study of the description, figures, and non-limiting examples in this document.

DESCRIPTION OF EXEMPLARY EMBODIMENTS

Figure 1:
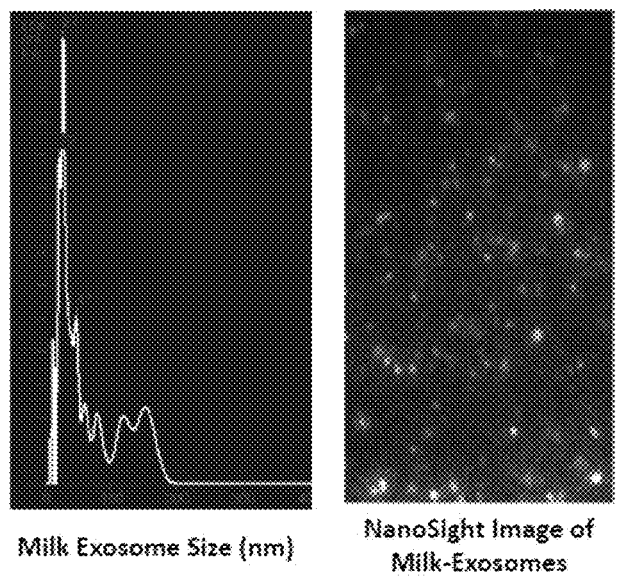
FIG. 1 includes a graph and an image showing the sizes of exosomes derived from bovine mature milk and colostrum as measured by a NanoSight Nanoparticle Tracking Instrument (Malvern Instruments, Westborough, Mass.), where, for the analysis, stock exosome suspension (6 mg/ml protein concentration) was diluted 20-50 fold in phosphate-buffered saline (PBS) and a total of 200 μl was analyzed.
Figure 2:
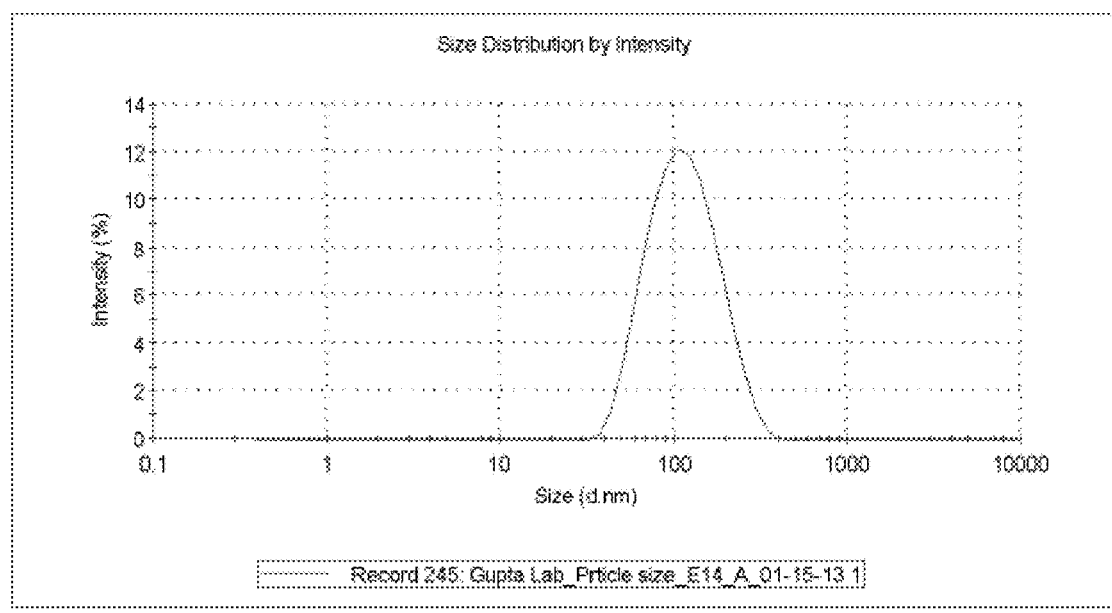
FIG. 2 includes a graph showing the size of exosomes derived from bovine mature milk and colostrum as measured by Zetasizer (Malvern Instruments Ltd., Worcestershire, UK), where exosomes were analyzed using 1 ml of the diluted suspension (1 mg/ml)
Figure 3:
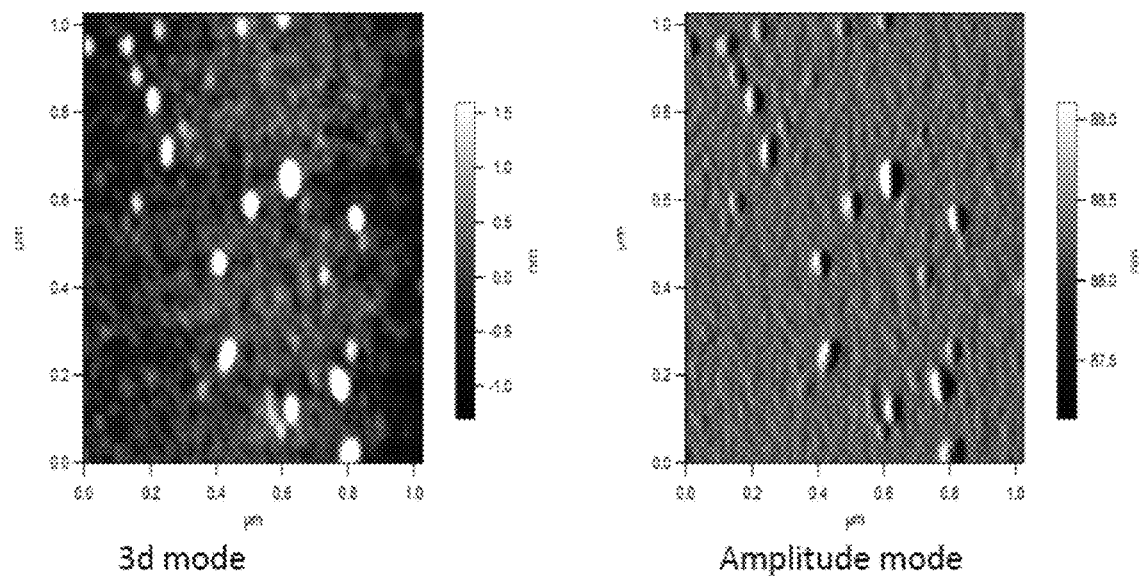
FIG. 3 includes images showing the size measurement of exosomes derived from bovine mature milk as measured by atomic force microscopy (AFM), where a diluted exosomal suspension was loaded on cleaned silicon wafers and air-dried for 30 min, and where Asylum MF-3D (Asylum Research, Oxford Instruments) AFM in 3D and tapping mode were used, silicon probes coated with aluminum coating (Force Constant=40 Nm-1; Resonant Frequency=300 kHz, Budget Sensors.com) were used for imaging, and where topographic height, amplitude and phase images were captured concurrently with a fixed force (<1 nN) with a scanning rate of 1 Hz.
Figure 4:
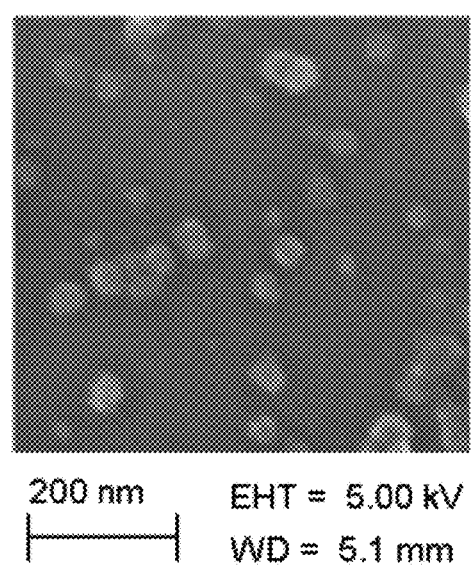
FIG. 4 includes an image showing the size measurement of exosomes derived from bovine mature milk measured by scanning electron microscopy (SEM), where a milk exosomal suspension was filtered through a 0.22 μm filter and loaded over clean silicon wafers and air-dried for 30 min, where silicon wafers were grounded using copper adhesive tape for conductivity, and where exosomes were imaged in Zeiss Supra 35 SEM under beam energies (5 kV) at 142,000× magnification.
Figure 5:
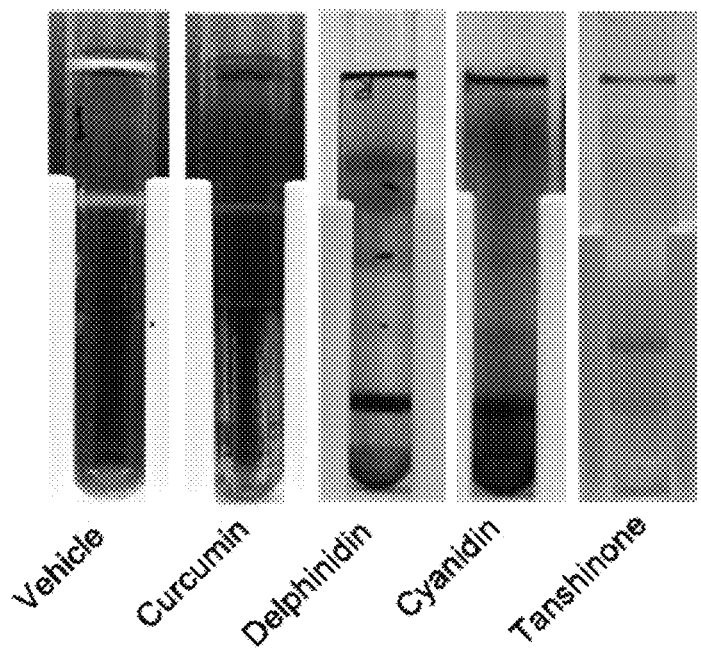
FIG. 5 includes an image showing separation of vehicle- and phytochemical agent-loaded bovine milk exosomes by sucrose density gradient, where the indicated agents were initially mixed with the exosomes in the presence of 10% ethanol, excess or unbound drug was removed by centrifugation at 10,000×g for 10 min, and the phytochemical agent-loaded exosomes were separated by centrifugation at 150,000×g on a sucrose gradient using a 41 Ti swing rotor.
Figure 6:
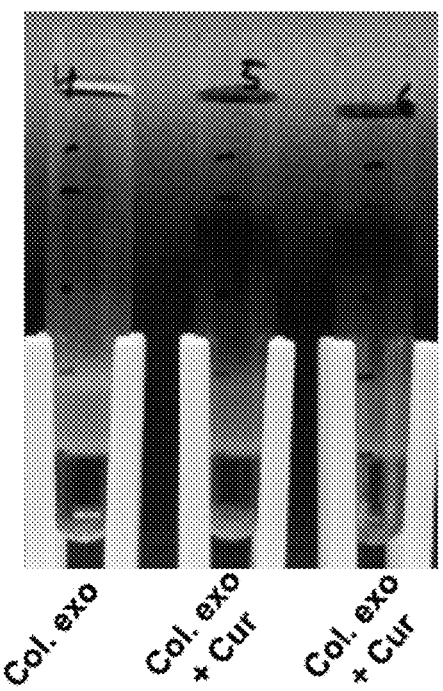
FIG. 6 is another image showing the separation of vehicle- and therapeutic agent-loaded bovine colostrum exosomes by sucrose density gradient, where curcumin was mixed with colostrum-derived exosomes in the presence of 10% ethanol, excess or unbound curcumin was removed by centrifugation at 10,000×g for 10 min, and the curcumin-loaded exosomes were separated by centrifugation at 150,000×g on a sucrose gradient using a 41 Ti swing rotor.
Figure 7:
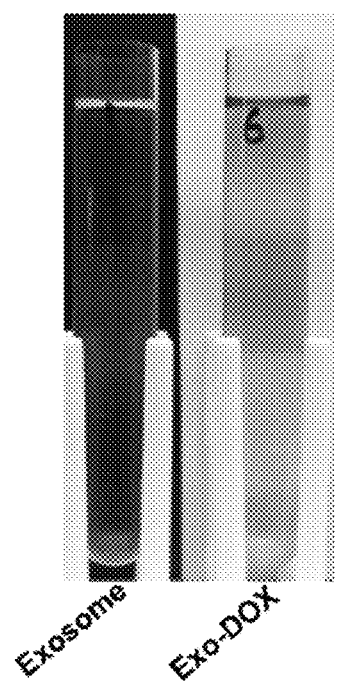
FIG. 7 includes an image showing separation of vehicle- and doxorubicin (DOX)-loaded bovine milk exosomes by sucrose density gradient, where DOX was mixed with the exosomes in the presence of 10% ethanol, excess or unbound DOX was removed by centrifugation at 10,000×g for 10 min, and the DOX loaded exosomes were separated by centrifugation at 150,000×g on a sucrose gradient using 41 Ti swing rotor.
Figure 8:
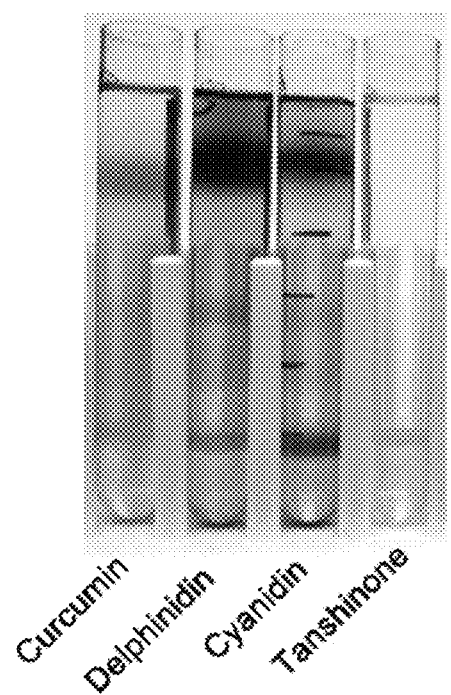
FIG. 8 includes another image showing the separation of phytochemical agent-loaded bovine colostrum exosomes by sucrose density gradient.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

In certain instances, microRNAs (miRNAs) disclosed herein are identified with reference to names assigned by the miRBase Registry (available at www.mirbase.org). The sequences and other information regarding the identified miRNAs as set forth in the miRBase Registry are expressly incorporated by reference as are equivalent and related miRNAs present in the miRBase Registry or other public databases. Also expressly incorporated herein by reference are all annotations present in the miRBase Registry associated with the miRNAs disclosed herein. Unless otherwise indicated or apparent, the references to the Sanger miRBase Registry are references to the most recent version of the database as of the filing date of this Application (i.e., mirBase 20, released June 2013).

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Microvesicles are naturally existing particles that are in the form of small assemblies of lipid particles, are about 30 to 1000 nm in size, and are not only secreted by many types of in vitro cell cultures and in vivo cells, but are commonly found in vivo in body fluids, such as blood, urine and malignant ascites. Indeed, microvesicles include, but are not limited to, particles such as exosomes, epididimosomes, argosomes, exosome-like vesicles, microparticles, promininosomes, prostasomes, dexosomes, texosomes, dex, tex, archeosomes, and oncosomes.

As noted above, microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies (MVBs) are formed by inward budding from the endosomal membrane and subsequent pinching off of small vesicles into the luminal space. The internal vesicles present in the MVBs are then released into the extracellular fluid as so-called exosomes.

As part of the formation and release of microvesicles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the microvesicles to potentially function as effective nanoparticle carriers of therapeutic agents. In this regard, the term "microvesicle" is used interchangeably herein with the terms "nanoparticle," "liposome," "exosome," "exosome-like particle," "nano-vector" and grammatical variations of each of the foregoing.

With further regard to the functional properties of microvesicles, it has now been discovered that milk, including colostrum, is not only a viable source of large quantities of microvesicles, but that microvesicles derived from milk can be used as an effective delivery vehicle for a number of therapeutic agents and can be used in a manner that retains the biological activity, including the bioavailability, of the therapeutic agents.

The presently-disclosed subject matter thus includes milk-derived microvesicle compositions that can be used to encapsulate a variety of therapeutic agents and are useful in the treatment of various diseases, including cancers. In some embodiments of the presently-disclosed subject matter, a microvesicle composition is provided that comprises an effective amount of a therapeutic agent encapsulated by a milk-derived microvesicle. In some embodiments, the therapeutic agent encapsulated by the milk-derived microvesicle is selected from a phytochemical agent or a chemotherapeutic agent.

The term "milk" is used herein to describe the opaque liquid that contains proteins, fats, lactose, and various vitamins and minerals and that is produced by the mammary glands of mature female mammals including, but not limited to, after the mammals have given birth to provide nourishment for their young. In this regard, in some embodiments, the term "milk" is further inclusive of colostrum, or the liquid that is secreted by the mammary glands of mammals at the time of parturition and that is rich in antibodies and minerals. In some embodiments, the compositions of the presently-disclosed subject matter are comprised of colostrum-derived microvesicles.

The phrase "milk-derived" or "colostrum-derived," when used in the context of a microvesicle derived from milk or colostrum, refers to a microvesicle that, by the hand of man, exists apart from its native environment and is therefore not a product of nature. In this regard, the phrases "milk-derived" microvesicles or "colostrum-derived" microvesicles is used interchangeably herein with the phrases "milk microvesicles" or "colostrum microvesicles," respectively to refer to microvesicles that have been isolated from milk or colostrum. Additionally, in some embodiments, the phrase "milk-derived" can be used interchangeably with the phrase "isolated from milk" to describe a microvesicle of the presently-disclosed subject matter that is useful for encapsulating therapeutic agents.

In some embodiments, the isolation of microvesicles is achieved by centrifuging raw (i.e., unpasteurized milk or colostrum) at high speeds to isolate the microvesicles. In one preferred embodiment, the microvesicles of the presently-disclosed subject matter are isolated in a manner that allows for the isolation of clinical-grade microvesicles in amounts greater than about 50 mg (e.g., greater than about 300 mg) of microvesicle protein per 100 ml of milk. In this regard, in some embodiments, a method of isolating a microvesicles is further provided that includes the steps of: obtaining an amount of milk (e.g., raw milk or colostrum); and subjecting the milk to a series of sequential centrifugations configured to yield greater than about 50 mg of exosomal protein per 100 ml of milk. In some embodiments, the sequential centrifugations yield greater than 300 mg of exosomal protein per 100 ml of milk. In some embodiments, the series of sequential centrifugations comprises a first centrifugation at 20,000×g at 4° C. for 30 min, a second centrifugation at 100,000×g at 4° C. for 60 min, and a third centrifugation at 120,000×g at 4° C. for 90 min. In some embodiments, the isolated microvesicles can then be stored at a concentration of about 5 mg/ml to about 10 mg/ml as such a concentration has been found to prevent coagulation and allow the isolated microvesicles to effectively be used for the encapsulation of one or more therapeutic agents. In some embodiments, the isolated microvesicles are passed through a 0.22 µm filter to remove any coagulated particles as well as microorganisms, such as bacteria.

The phrase "encapsulated by a microvesicle," or grammatical variations thereof is used herein to refer to microvesicles whose lipid bilayer surrounds a therapeutic agent. For example, a reference to "microvesicle curcumin" refers to a microvesicle whose lipid bilayer encapsulates or surrounds an effective amount of curcumin. In some embodiments, the encapsulation of various therapeutic agents within microvesicles can be achieved by mixing the one or more of the phytochemical agents or chemotherapeutic agents with isolated microvesicles in a suitable solvent, such as ethanol. After a period of incubation sufficient to allow the therapeutic agent to become encapsulated during the incubation period, the microvesicle/therapeutic agent mixture is then subjected to a low-speed centrifugation (e.g., 10,000×g) to remove any unbound therapeutic agent and one or more high-speed centrifugation centrifugations to isolate the microvesicles encapsulating the therapeutic agents.

As used herein, the term "therapeutic agent" is used to refer to an agent that is capable of "treating" a disease, as defined herein below. As noted above, in some embodiments, the therapeutic agent can comprise a phytochemical agent or a chemotherapeutic agent.

The term "phytochemical agent" refers to a non-nutritive plant-derived compound, or an analog thereof, that is capable of "treating" a disease, as defined herein below. Examples of phytochemical agents include, but are not limited to compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables. Table 1 provides a list of specific phytochemical agents that are exemplary of the broader classes of phytochemical agents described herein above.

In some embodiments, the phytochemical agent is selected from curcumin, demethoxycurcumin, delphinidin, cyanidin, withaferin A, tanshinone, a mixture of anthocyanidins (e.g., bilberry anthocyanidins), or combinations thereof. In some embodiments, the phytochemical agent is a bilberry anthocyanidin mixture, punicalagin, tanshinone II, or combinations thereof. In some embodiments, the phytochemical agent is curcumin or Withaferin A. In some embodiments, the phytochemical agent is a bilberry anthocyanin mixture which includes, in certain embodiments, a mixture of five anthocyanidins isolated from anthocyanin-enriched bilberry extract following acid hydrolysis and purification by solid-phase or solvent-solvent extraction. In some embodiments, the mixture of five anthocyanidins is a mixture of delphinidin, cyanidin, malvidin, peonidin, and petunidin.

TABLE 1

List of Exemplary Phytochemical Agents.

| PHENOLIC COMPOUNDS | | TERPENES | BETALAINS |
|---|---|---|---|
| Monophenols | Flavonoids (polyphenols) | Carotenoids | Betalains |
| Apiole | Flavonols | (tetraterpenoids) | Betacyanins |
| Carnosol | Quercetin | Carotenes | Betanin |
| Carvacrol | Gingerol | α-Carotene | Isobetanin |
| Dillapiole | Kaempferol | β-Carotene | Probetanin |
| Rosemarinol | Myricetin | γ-Carotene | Neobetanin |
| Phenolic acids | Rutin | δ-Carotene | Betaxanthins |
| Ellagic acid | Isorhamnetin | Tocotrienols | Indicaxanthin |
| Gallic acid | Flavanones | Tocopherols | Vulgaxanthin |
| Salicylic acid | Hesperidin | Lycopene | |
| Tannic acid | Naringenin | Neurosporene | |
| Vanillin | Silybin | Phytofluene | |
| Capsaicin | Eriodictyol | Phytoene | |
| Curcumin | Flavones | Xanthophylls | ORGANOSULFIDES |
| Plumbagin | Apigenin | Canthaxanthin | Dithiolthiones |
| Hydroxycinnamic | Tangeritin | Cryptoxanthin | Sulphoraphane |
| acids | Luteolin | Zeaxanthin | Thiosulphonates |
| Caffeic acid | Flavan-3-ols | Astaxanthin | Allyl methyl trisulfide |
| Chlorogenic acid | Catechins | Lutein | Dialyl sulfide |
| Cinnamic acid | Gallocatechin | Rubixanthin | |
| Ferulic acid | Epicatechin | Monoterpenes | |
| Coumarin | Epigallocatechin | Limonene | |
| Lignans | Epigallocatechin gallate | Perillyl alcohol | |
| (phytoestrogens) | Epicatechin-gallate | Saponins | INDOLES, |
| Silymarin | Theaflavin | Lipids | GLUCOSINOLATES |
| Matairesinol | Theaflavin-gallate | Phytosterols | Indole-3-carbinol |
| Secoisolariciresinol | Theaflavin-digallate | Campesterol | sulforaphone |
| Pinoresinol | Thearubigins | β-Sitosterol | 3,3'-Diindolylmethane |
| Lariciresinol | Anthocyanins | γ-Sitosterol | Sinigrin |

TABLE 1-continued

List of Exemplary Phytochemical Agents.

| | | | |
|---|---|---|---|
| Tyrosol esters | & Anthocyanidins | Stigmasterol | Allicin |
| Tyrosol | Pelargonidin | Tocopherols | Alliin |
| Hydroxytyrosol | Peonidin | ω-3,6,9 fatty acids | Allyl isothiocyanate |
| Oleocanthal | Cyanidin | γ-linolenic acid | Piperine |
| Oleuropein | Delphinidin | Triterpenoid | |
| Stilbenoids | Malvidin | Withaferin A | |
| Resveratrol | Petunidin | Oleanolic acid | |
| Pterostilbene | Isoflavones (phytoestrogens) | Ursolic acid | |
| Piceatannol | Daidzein | Betulinic acid | |
| Hydrolyzable Tannins | Genistein | Moronic acid | |
| Punicalagins | Equol | Curcurbitacins | |
| | Glycitein | Lupeol | |
| | Dihydroflavonols | | |
| | Chalcones | | |
| | Coumestans | | |
| | Coumestrol | | |

As also noted herein above, in some embodiments of the presently-disclosed subject matter, the therapeutic agent that is encapsulated within the exosome is a chemotherapeutic agent. Examples of chemotherapeutic agents that can be used in accordance with the presently-disclosed subject matter include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor *vinca* alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, Mass.); or YONDELIS® (Johnson & Johnson, New Brunswick, N.J.). In some embodiments, the chemotherapeutic agent that is encapsulated by an exosome in accordance with the presently-disclosed subject matter is selected from retinoic acid, 5-fluorouracil, vincristine, actinomycin D, adriamycin, cisplatin, docetaxel, doxorubicin, and taxol. In some embodiments, the chemotherapeutic agent is doxorubicin, docetaxel, paclitaxel, or a combination thereof.

In some embodiments, the microvesicle composition described herein further includes one or more microRNAs (miRNAs), either by virtue of being present in the microvesicles upon their isolation or by virtue of artificially encapsulating one or more miRNAs into the microvesicles subsequent to their initial isolation. As would be recognized by those skilled in the art, miRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression. There are three forms of miRNAs existing in vivo, primary miRNAs (pri-miRNAs), premature miRNAs (pre-miRNAs), and mature miRNAs. Primary miRNAs are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length. In some embodiments, the miRNAs encapsulated by the microvesicles of the presently-disclosed subject matter are selected from miR-155, which is known to act as regulator of T- and B-cell maturation and the innate immune response, or miR-223, which is known as a regulator of neutrophil proliferation and activation.

In some embodiments of the presently-disclosed subject matter, pharmaceutical compositions included the milk-derived exosomes are further provided. In some embodiments, a pharmaceutical composition is provided that comprises a milk-derived microvesicle composition disclosed herein and a pharmaceutical vehicle, carrier, or excipient. In some embodiments, the pharmaceutical composition is pharmaceutically-acceptable in humans. Also, as described further below, in some embodiments, the pharmaceutical composition can be formulated as a therapeutic composition for delivery to a subject.

A pharmaceutical composition as described herein preferably comprises a composition that includes pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

The compositions can further be formulated as topical semi-sold ointment or cream formulations can contain a concentration of the presently-described microvesicle compositions in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic. In some embodiments, such ointment or cream formulations can be used for trans-dermal delivery of the pharmaceutical compositions described herein or for delivery to organs such as vagina or cervix in women.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the microvesicle compositions of the presently-disclosed subject matter can also be formulated as rectal compositions, such as suppositories or retention enemas, e.g., containing conventional suppository bases such as cocoa butter or other glycerides. Further, the microvesicle compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently-disclosed subject matter, are methods for modifying an immune response in a subject. As used herein, the term "immune response" includes responses which are caused, at least in part, or mediated, by the immune system of an individual. In some embodiments, a method for modifying an immune response is provided that comprises administering to a subject in need thereof an effective amount of a microvesicle composition of the presently-disclosed subject matter, wherein the microvesicle included in the composition is derived from milk. In some embodiments of the methods for modifying an immune response, the therapeutic agent is selected from a phytochemical agent or an miRNA. For example, in some embodiments, the therapeutic agent is a phytochemical agent and an effective amount of curcumin, demethoxycurcumin, delphinidin, cyanidin, withaferin A, tanshinone, bilberry anthocyanidins, or combinations thereof are administered to a subject to thereby modify and immune response. As another example, in some embodiments, the therapeutic agent is an miRNA and an effective amount of miR-155, miR-223, or a combination thereof is administered to a subject to thereby modify an immune response.

For administration of a therapeutic composition as disclosed herein (e.g., a milk-derived microvesicle encapsulating a therapeutic agent), conventional methods of extrapolating human dosage based on doses administered to a murine animal model can be carried out using the conversion factor for converting the mouse dosage to human dosage: Dose Human per kg=Dose Mouse per kg×$\frac{1}{12}$ (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally, intravenously, intranasally, or intraperitoneally to thereby treat a disease or disorder.

Regardless of the route of administration, the compositions of the presently-disclosed subject matter typically not only include an effective amount of a therapeutic agent, but are typically administered in amount effective to achieve the desired response. As such, the term "effective amount" is used herein to refer to an amount of the therapeutic composition (e.g., a microvesicle encapsulating a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

With further respect to the therapeutic methods described herein, included the above-described methods of modifying an immune response, in some embodiments of the therapeutic methods, administering a milk-derived microvesicle composition of the presently-disclosed subject matter reduces an amount of an inflammatory cytokine in a subject. In some embodiments, the inflammatory cytokine can be interleukin-1β (IL-1β), tumor necrosis factor-alpha (TNF-α), interferon-γ (IFN-γ), or interleukin-6 (IL-6). In some embodiments, administering the composition reduces an amount of NF-κB signaling in a subject.

Various methods known to those skilled in the art can be used to determine a reduction in the amount of inflammatory cytokines or an amount of NF-κB signaling in a subject. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, Calif.). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

With further regard to determining levels of inflammatory cytokines or NF-κB signaling in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of increase in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory cytokines in a subject can be compared to control level of inflammatory cytokines, and an amount of inflammatory cytokines of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Still further provided, in some embodiments, are methods for treating a cancer. In some embodiments, a method for treating a cancer is provided that comprises administering to a subject in need thereof an effective amount of an milk-derived microvesicle composition of the presently-disclosed subject matter (i.e., where the microvesicle encapsulates a therapeutic agent). In some embodiments, the therapeutic agent encapsulated within the microvesicle and used to treat the cancer is selected from a phytochemical agent, a chemotherapeutic agent, and an miRNA molecule, such as those described herein above, as such agents have been found to be particularly useful in the treatment of cancer.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As further non-limiting examples of the treatment of a cancer by a composition described herein, treating a cancer can include, but is not limited to, killing cancer cells, inhibiting the development of cancer cells, inducing apoptosis in cancer cells, reducing the growth rate of cancer cells, reducing the incidence or number of metastases, reducing tumor size, inhibiting tumor growth, reducing the available blood supply to a tumor or cancer cells, promoting an immune response against a tumor or cancer cells, reducing or inhibiting the initiation or progression of a cancer, increasing the lifespan of a subject with a cancer, or inhibiting or reducing the formation of DNA adducts by chemical carcinogens.

In some embodiments of the presently-disclosed subject matter, a method for treating a cancer is provided wherein the treating comprises inhibiting or reducing the formation of DNA adducts. The formation of DNA adducts (i.e. carcinogens covalently bound to DNA) is widely considered a prerequisite for the initiation and progression of cancer development. Many carcinogens are known to induce the formation of DNA adducts (Hemminki, 1993) and the presence of DNA adducts in humans has been strongly correlated with an increased risk for cancer development (Santella, 1997). For example, human studies have shown a higher accumulation of tissue DNA adducts in cigarette smokers than in non-smokers or individuals who have never smoked, indicating that DNA adduct formation is a viable target for the treatment of cancer.

As used herein, the term "cancer" refers to all types of cancer or neoplasm or malignant tumors found in animals, including leukemias, carcinomas, melanoma, and sarcomas. By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of breast cancer, uterine cancer, lung cancer, prostate cancer, ovarian cancer, cervical cancer, and pancreatic cancer.

In some embodiments, the compositions of the presently-disclosed subject matter can further be used in a method of treating an inflammatory disorder that includes administering an effective amount of the composition to a subject in need of treatment for an inflammatory disorder. As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, microorganisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to atherosclerosis; arthritis; inflammation-promoted cancers; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease.

In yet further embodiments of the presently-disclosed subject matter, the compositions can be used to treat degenerative diseases, such as Alzheimer's disease or Parkinson's disease. In other embodiments, the compositions can be used to treat diabetes.

As reflected herein above, the compositions and methods of the presently-disclosed subject matter thus provide the capability of using milk-derived microvesicles as a carrier for both natural and synthetic chemopreventive and chemotherapeutic agents. Furthermore, by using the microvesicles as a carrier, the compositions and methods provide a means to enhance oral bioavailability of the encapsulated agents by minimizing destruction of the agent in the gut and liver first-pass effect and also a means to improve agent delivery across the blood brain barrier (BBB). Additionally, the compositions and methods described herein provide the added benefits of using the compositions to: improve the immune system in cancer patients undergoing chemotherapy; provide natural compound-loaded milk and colostrum exosomes as adjuvant therapy to increase efficacy of chemo-drugs; provide natural product-loaded milk and colostrum exosomes as preventive therapies post-chemotherapy to prevent or delay relapse or recurrence of secondary cancer; supplement commercial milk formula with exosomes derived from mother's milk or cow's milk/colostrum; boost the immune system of infants and adults by milk exosomes utilizing the in-built immune factors; improve the immune system in subjects with inflammatory disease and viral infections including common cold since immune system is compromised severely in these subjects; and increase the solubility and stability of the therapeutic agents, including the solubility and stability of the agents within subjects.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1—Isolation and Storage of Milk-Derived Exosomes

Numerous centrifugation protocols were assessed using raw bovine milk, and isolated exosomes were measured for their protein content, yield, and their sizes using a NanoSight Nanoparticle Tracking Instrument (Malvern Instruments, Westborough, Mass.). In one preferred procedure, a sequential centrifugation of raw milk or colostrum was employed that included centrifugation at 20,000×g at 4° C. for 30 min, 100,000×g at 4° C. for 60 min and 120,000×g at 4° C. for 90 min. Those conditions yielded, on average, greater than 300 mg exosomal protein/100 ml milk (Tables II and III) and yielded exosomes that were 30-100 nm size as assessed by NanoSight (FIGS. 1-4). Several gallons of raw milk were subsequently processed and it was found that milk exosomes were isolated in tens and hundreds gram quantities or could be isolated in kilogram quantities, if desired. Additionally, it was found that exosomes isolated from bovine colostrum resulted in 1.5-fold higher yields of exosomes than raw bovine milk. In this regard, and without wishing to be bound by any particular theory, it was believed that since colostrum contained higher levels of immune-related miRNAs than milk, colostrum exosomes could render a higher immune response or modulation than raw mature milk-derived exosomes. Reproducibility was also established in several preparations of exosomes made from both bovine milk and colostrum.

TABLE II

Yield of exosomes isolated from bovine mature milk and colostrum.

| Experiment | Weight of pellet (g)/ 100 ml milk | Exosomal protein (mg)/100 ml milk |
|---|---|---|
| Exp # 1 | 2.7 | 302 |
| Exp # 2 | 2.5 | 365 |
| Exp # 3 | 2.3 | 265 |
| Exp # 4 | 2.6 | 295 |
| Exp # 5 | — | 343 |
| Average ± SD | 2.53 ± 0.17 | 314 ± 39 |

TABLE III

Dry mass in milk exosomal pellet.

| Sample No. | Pellet wt. (wet) | Pellet wt. (Dry) | % Dry wt. |
|---|---|---|---|
| Sample No. 1 | 3.02 | 0.71 | 23.5 |
| Sample No. 2 | 2.75 | 0.65 | 23.7 |
| Sample No. 3 | 2.96 | 0.72 | 24.4 |
| Sample No. 4 | 2.48 | 0.60 | 24.2 |
| Average ± SD | 2.8 ± 0.2 | 0.67 ± 0.06 | 23.95 ± 0.4 |

Figure 9:
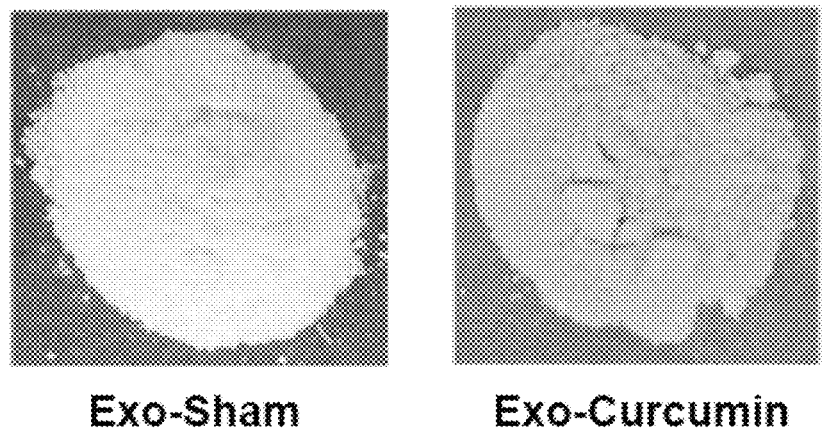
FIG. 9 includes images showing a dried powder of bovine milk-derived exosomes and curcumin-loaded bovine milk-derived exosomes, where the exosomes alone (5 mg/ml) and the curcumin-loaded exosomes (5 mg/ml protein containing 12% curcumin) were suspended in phosphate-buffered-saline (PBS) and dried by a nanospray apparatus using a 0.45 μM pore size nozzle.

Storage of exosomes was analyzed to identify conditions for minimizing coagulation. Systematic efforts showed that the milk-derived exosomes if stored at −80° C. at less than or equal to 6 mg exosomal protein/ml PBS remained largely free of coagulated particles, and were observed to be stable in terms of their biological activity and size for months. Similar results were also observed when stored in liquid nitrogen and in 50% glycerol at −80° C. Moreover, conversion of milk exosomes to dry powder by Buchi Nano Spray (BÜCHI Labortechnik AG, Switzerland) drying showed no change in the particle size and minimal loss of biologic activity (see, e.g., FIG. 9)

Example 2—Milk and Colostrum Exosomes as Drug Carrier

Figure 10:
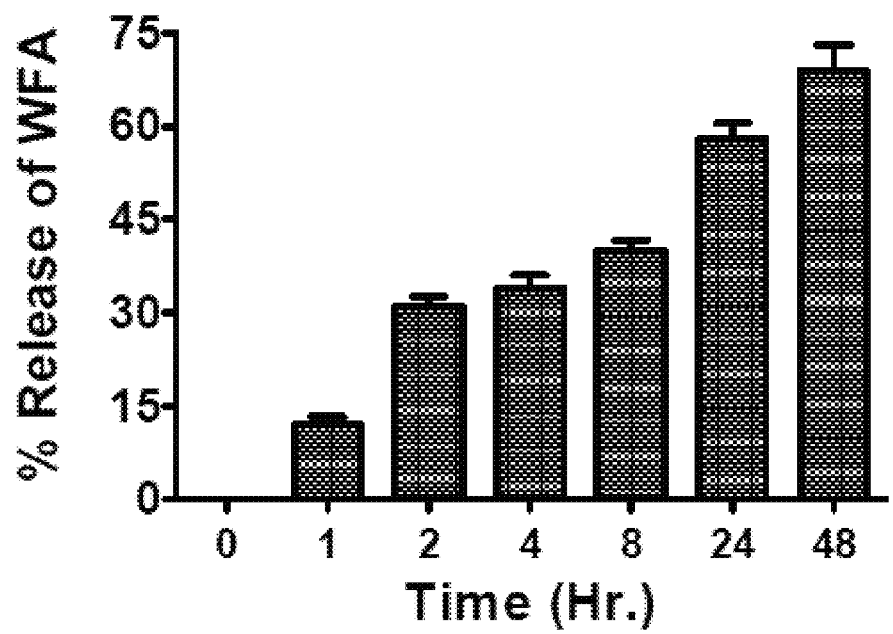
FIG. 10 includes a graph showing the kinetics of therapeutic agent release in vitro from withaferin A (WFA) loaded milk-exosomes, where the release study was done using dialysis tubes against buffer containing the surfactant, Tween-80 (0.02%) at 37° C., and where WFA extracted from the residual material was found to be stable during the workup, based on high pressure liquid chromatography analysis.
Figure 11A:
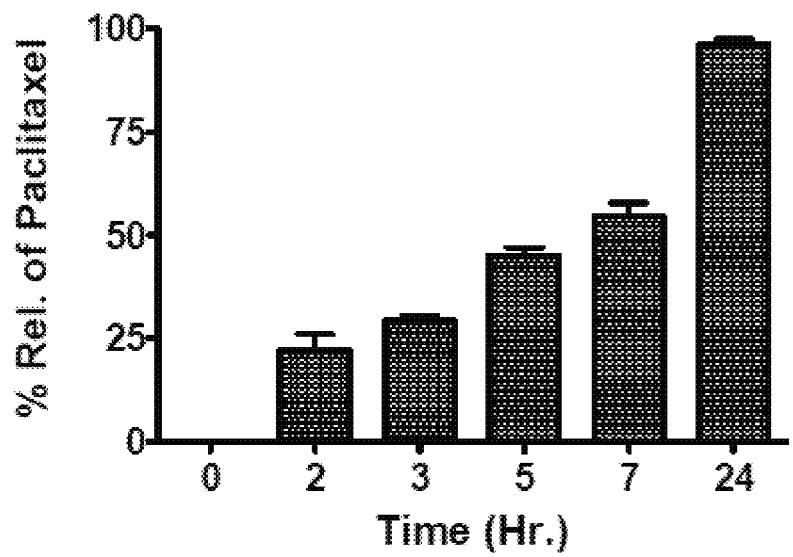
FIGS. 11A-11B includes graphs showing the kinetics of therapeutic agent release in vitro from chemotherapeutic agent-loaded milk exosomes, where the release study was done using dialysis tubes against buffer containing the surfactant, Tween-80 (0.02%) at 37° C., and where the chemotherapeutic agents, paclitaxel (FIG. 11A) and docetaxel (FIG. 11B), extracted from the residual material were found to be stable during the workup, based on the UV spectral analysis.
Figure 11B:
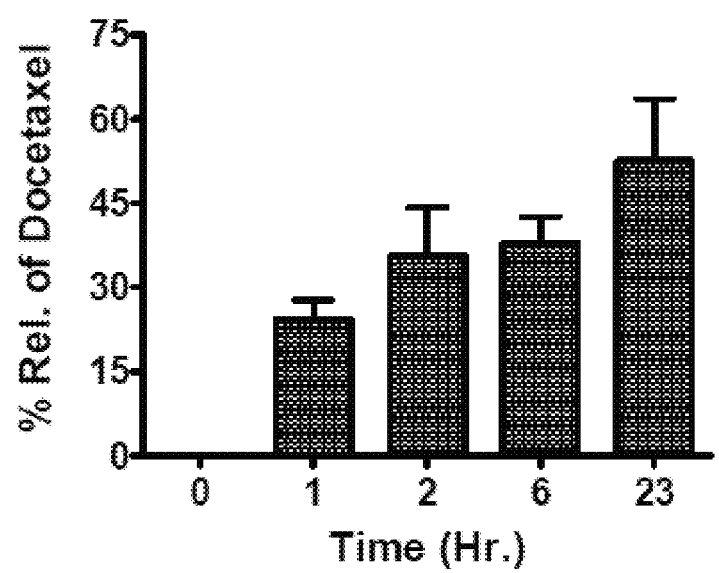

Several procedures were developed to load therapeutic agents onto the milk- or colostrum-derived exosomes. Those procedures included i) suspending therapeutic agents in PEG-400, mixing with milk-derived exosomes, followed by low-speed centrifugation; ii) dissolving therapeutic agents in ethanol, mixing with milk- or colostrum-derived exosomes, low-speed centrifugation (10,000×g) to remove unbound therapeutic agent, and finally high-speed centrifugation; and iii) mixing therapeutic agents in ethanol with 100,000 whey (obtained after the 100,000×g centrifugation), low-speed centrifugation and finally 120,000×g centrifugation. In one preferred embodiment, incubation of exosomes in PBS with test agents in the presence of 10% ethanol or 10% ethanol:acetonitrile (1:1) allowed for increased loading of therapeutic agents into the exosomes. The agents utilized in those studies included curcumin, withaferin A, demethoxycurcumin, delphinidin, cyanidin, a native mixture of (five) anthocyanidins from bilberry, punicalagin, and tanshinone II. The chemotherapeutic agents doxorubicin, paclitaxel, and docetaxel were also loaded in the exosomes. In this regard, it was observed that the exosomes accepted both hydrophobic (paclitaxel, docetaxel, curcumin, withaferin A, tanshinone II) and hydrophilic agents (berry anthocyanidins, punicalagin) with a loading efficiency of 4% to 65% with respect to exosomal proteins, as determined by measurement of the drug and exosomal protein contents (Tables IV and V). Sucrose density gradient ultracentrifugation confirmed the presence of drugs embedded in the exosomes (FIGS. 5-8). When tested for in vitro release using dialysis tubes against buffer containing the surfactant, Tween-80 [47] at 37° C., PAC and WFA were released time-dependently—20%, 43% and 70% PAC in 2, 6 and 19 h, and 12%, 40% and 58% WFA in 1, 4, and 24 h, respectively (FIGS. 10, 11A, and 11B). Similarly, the berry anthocyanidins were found to be released time-dependently—20%, 43% and 70% in 2, 6 and 19 h, respectively, with SD of less than 10%. Further, the anthocyanidins extracted from the residual material showed the same UV spectral profile as the starting material indicating that the compounds were stable in the exosomal formulation.

TABLE IV

Dose-dependent loading of bovine milk-derived exosomes with lipophilic (withaferin A) and hydrophilic (anthocyanidins) chemopreventive agents.

| Chemopreventive | Sample # | Amount used (mg) | | % Drug load |
|---|---|---|---|---|
| | | Agent | Exosomal protein | |
| Withaferin A | A | 5 | 50 | 3.8 |
| | B | 10 | 50 | 8.6 |
| | C | 20 | 50 | 31.4 |
| | D | 25 | 50 | 44.8 |
| Anthocyanidins | A | 3 | 30 | 3.4 |
| | B | 6 | 30 | 9.2 |
| | C | 8 | 30 | 23.0 |
| | D | 10 | 30 | 25.1 |

TABLE V

Dose-depended loading of bovine milk-derived exosomes with chemotherapeutic drugs, paclitaxel and docetaxel.

| Chemotherapeutic agents | Sample # | Amount used (mg) | | % Drug load |
|---|---|---|---|---|
| | | Chemo. drug | Exosomal protein | |
| Paclitaxel | A | 3 | 30 | 15.7 |
| | B | 6 | 30 | 20.3 |
| | C | 9 | 30 | 14.9 |
| | D | 12 | 30 | 36.6 |
| | E | 18 | 30 | 64.6 |
| Docetaxel | A | 3 | 30 | 6.0 |
| | B | 6 | 30 | 17.7 |
| | C | 9 | 30 | 34.5 |
| | D | 12 | 30 | 49.1 |
| | E | 18 | 30 | 55.1 |

Example 3—Uptake of Milk and Colostrum Exosomes by Human Cancer Cells

Figure 12:
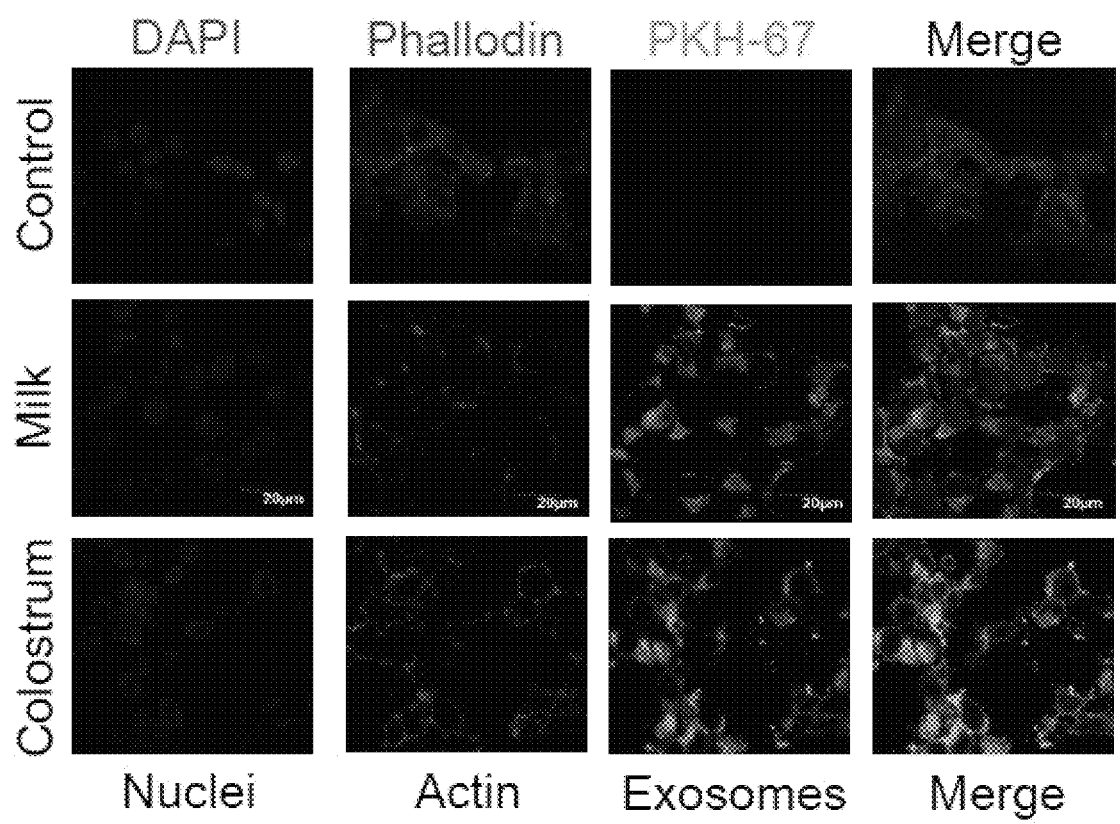
FIG. 12 includes images showing the uptake of bovine mature milk- and colostrum-derived exosomes by human lung cancer cells, where 500 μg of the PKH67-labeled bovine milk and colostrum exosomes, or exosome alone were added per 40,000 H1299 cells and incubated at 37° C. for 4 h, where the uptake of the fluorescently-labeled exosomes were detected by confocal microscopy, and where alexa flour-phalloidin 549 was used to detect actin filaments, DAPI was used for the nucleus of the H1299 cells, and PKH67 was used to label the exosomes.
Figure 13:
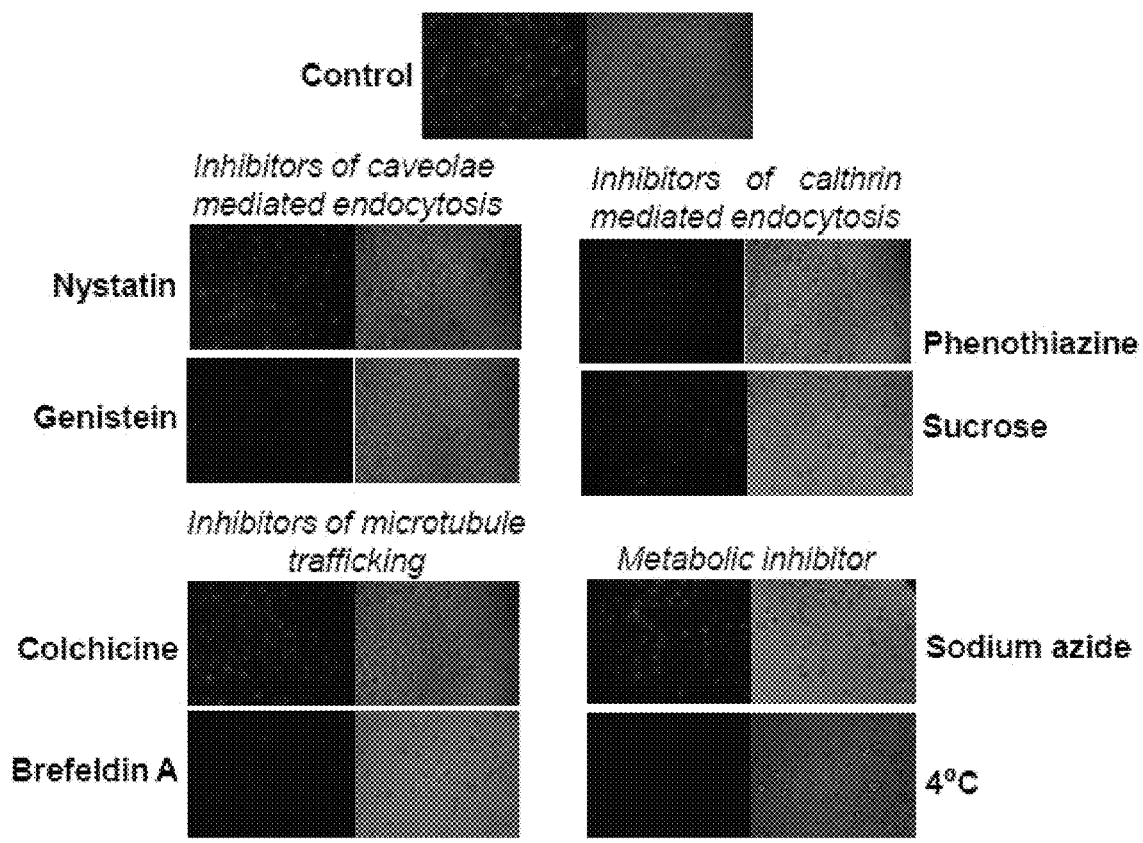
FIG. 13 includes images showing the effect of endocytosis inhibitors on the uptake of milk-derived exosomes, where human lung cancer H1299 cells were treated with the indicated endocytosis inhibitors for 2 hrs, followed by PKH-26 labeled exosomes (50 μg exo protein/ml) for 4 hrs, and where cells were imaged using an AMG EVOS fluorescent microscope at 20× magnification, while the gray images indicate cells in the field and were taken at bright field.
Figure 14:
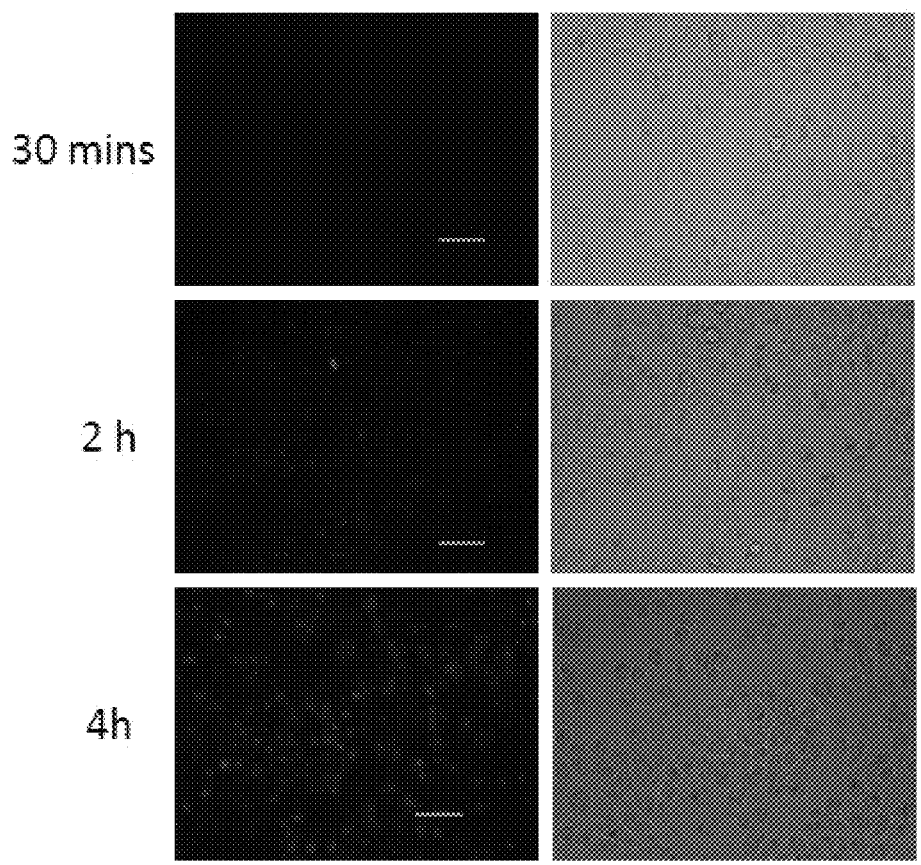
FIG. 14 includes images showing the effect of time on uptake of milk exosomes, where human lung cancer (H1299) cells were treated with PKH-26 labeled exosomes (50 μg exo protein/ml) for the indicated time, and where cells were imaged using a AMG EVOS fluorescent microscope at 20× magnification, with the gray images were taken at bright field.
Figure 15:
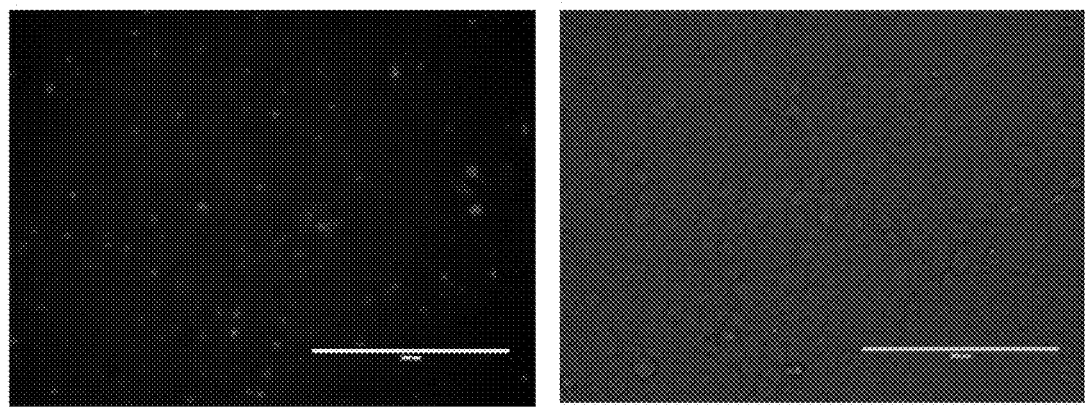
FIG. 15 includes images showing siRNA loading into milk-derived exosomes, where siRNA (BLOCK-iT™ Alexa Fluor® Red Fluorescent Control, Invitrogen) was used to load into milk exosome electroporation buffer, where the siRNA and milk exosome mixture was electroporated at 400 mV with the pulse time of 10-15 ms, and where the electroporated mixture was applied onto H1299 lung cancer cells and transfection efficiency visualized after 24 h under AMG EVOS fluorescent microscope at 10× magnification (scale 200 μm), with the gray images being captured under bright field.

To analyze whether exosomes derived from milk or colostrum would be sufficiently taken up by cells, including cancer cells, exosomes labeled with a fluorescent marker were incubated with human cancer cells in vitro under standard cell culture conditions. Briefly, milk- and colostrum-derived exosomes 500 µg (6 mg/ml protein) were incubated with PKH67 solution in Diluent C (final concentration during labeling: 5×10$^6$M) and incubated for 3 min to ensure homogeneous staining. The labeling step was stopped by the addition of an equal volume of FBS for 1 min, followed by an equal volume of complete DMEM medium. Labeled exosomes were washed with PBS using a molecular cutoff filter (100,000 MWCO), and the exosomes were re-suspended in 100 µl of FBS. Exosomes labeled with PKH67 were incubated with H1299 lung cancer cells at 37° C. for 4 hrs. After washing three times with PBS, cells were fixed and stained with alexa flour-phalloidin 549 to detect actin filaments and DAPI for the nucleus of the H1299 cells. Upon analysis of the results, it was observed that milk- and colostrum-derived exosomes labeled with the green fluorescent cell linker (PKH-67) were efficiently incorporated into human lung cancer H1299 cells in cell culture (FIG. 12), with maximal incorporation occurring after 4 to 8 hrs (FIG. 14). It was further observed that siRNA molecules could be efficiently loaded into milk-exosomes by electroporation, and that such siRNA-loaded exosomes could be used to transfect the H1299 human lung cancer cells (FIG. 15). Additionally, the effect of endocytosis inhibitors in the uptake of the exosomes was assessed by treating H1299 human lung cancer cells with endocytosis inhibitors for 2 hrs prior to incubation of the cells with PKH-26 labeled exosomes. It was subsequently observed that inhibitors of caveolae-mediated endocytosis, inhibitors of calthrin-mediated endocytosis, inhibitors of microtubule trafficking, and metabolic inhibitors each reduced uptake of the milk- and colostrum-derived exosomes (FIG. 13).

Figure 16:
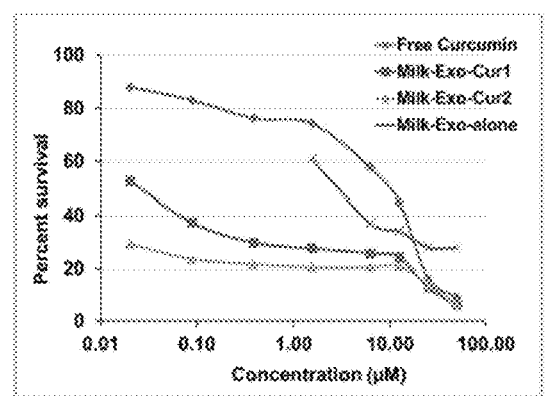
FIG. 16 includes graphs showing the antiproliferative activity of curcumin-loaded milk exosomes versus free curcumin in human lung cancer A549 (left graph) and H1299 (right graph) cells, where Exo-Cur1 exosomal protein concentration (μg/ml) was changed in parallel with curcumin concentration, and where Exo-Cur2, exosomal protein concentration were maintained constant (100 μg/ml)
Figure 16:
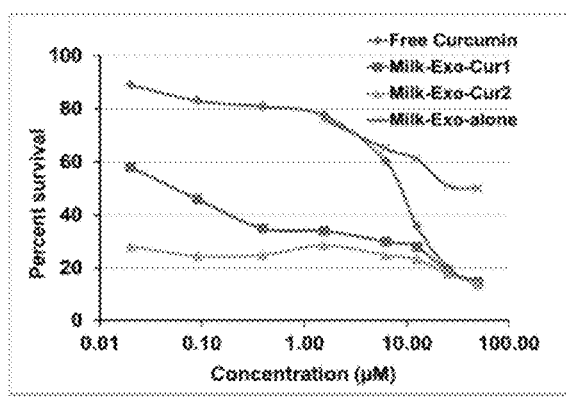
Figure 17:
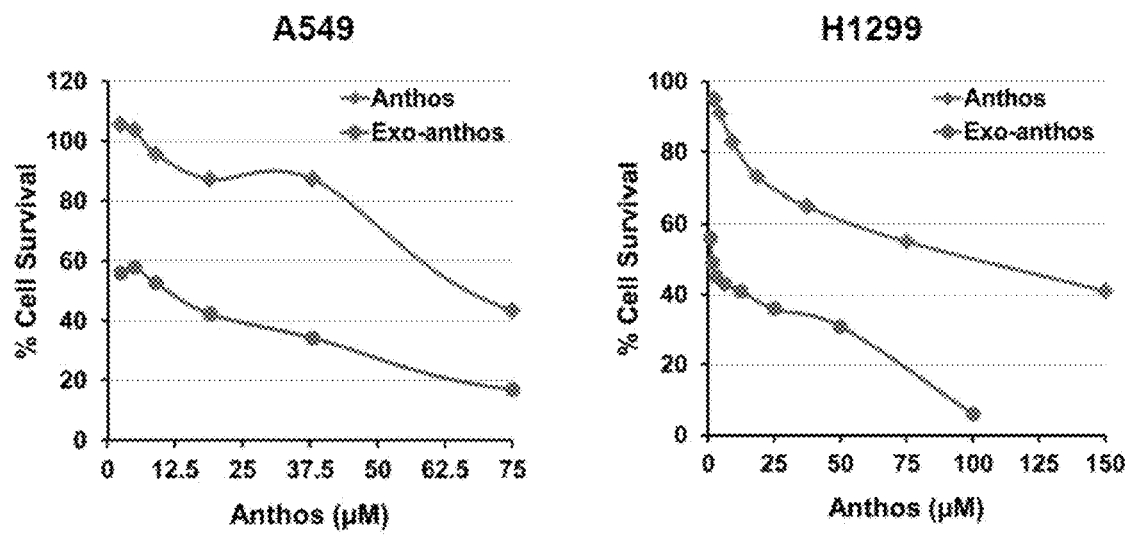
FIG. 17 includes graphs showing the antiproliferative activity of bilberry anthocyanidins-loaded milk exosomes versus free anthocyanidins in human lung cancer A549 and H1299 cells, where anthocyanidins-loaded milk exosomes and exosomal protein concentration were maintained constant (100 μg/ml).
Figure 18:
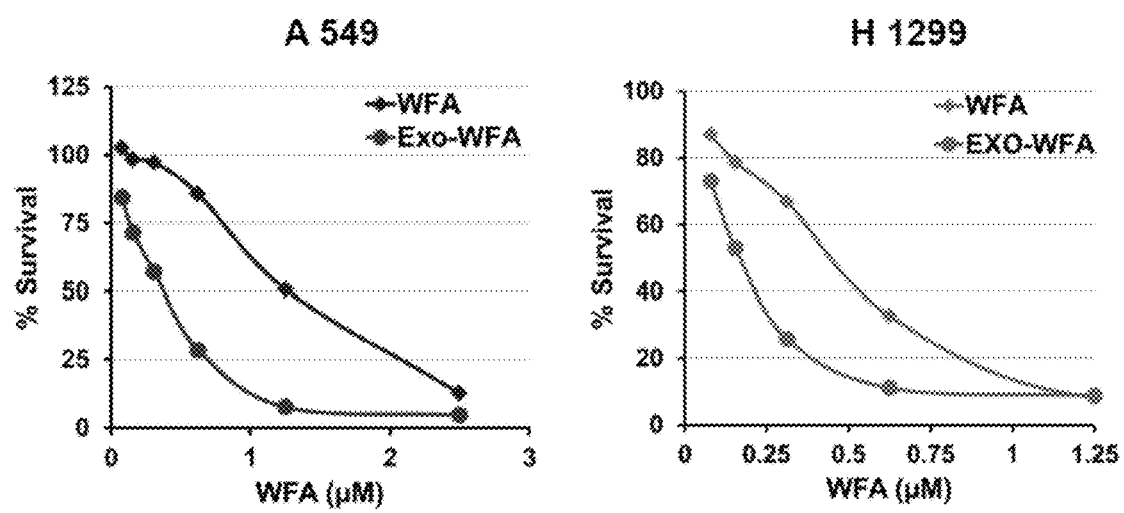
FIG. 18 includes graphs showing the antiproliferative activity of withaferin A-loaded milk exosomes versus free withaferin A in human lung cancer A549 and H1299 cells, where withaferin A-loaded milk exosomes and exosomal protein concentration were maintained constant (50 μg/ml).
Figure 19:
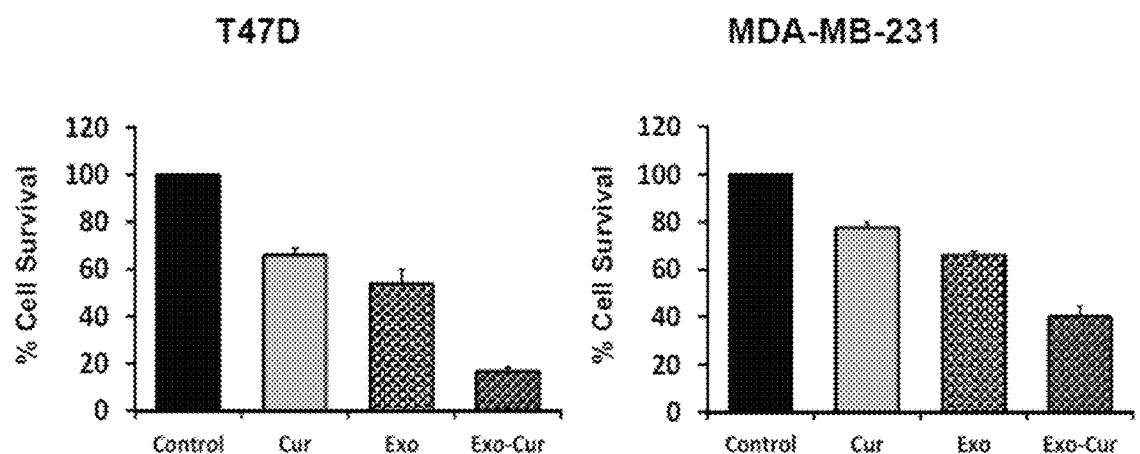
FIG. 19 includes graphs showing the antiproliferative activity of curcumin-loaded milk exosomes versus free curcumin in human breast cancer T47D (left graph) and MDA-MB-231 (right graph) cells, where breast cancer T47D and MDA-MB-231 cells were treated with either 12.5 μM curcumin or 45 μg/ml milk exosomes or curcumin-loaded milk exosomes (12.5 curcumin at 45 μg/ml exosomal protein), and where percent cell survival was analyzed by MTT assay.
Figure 20:
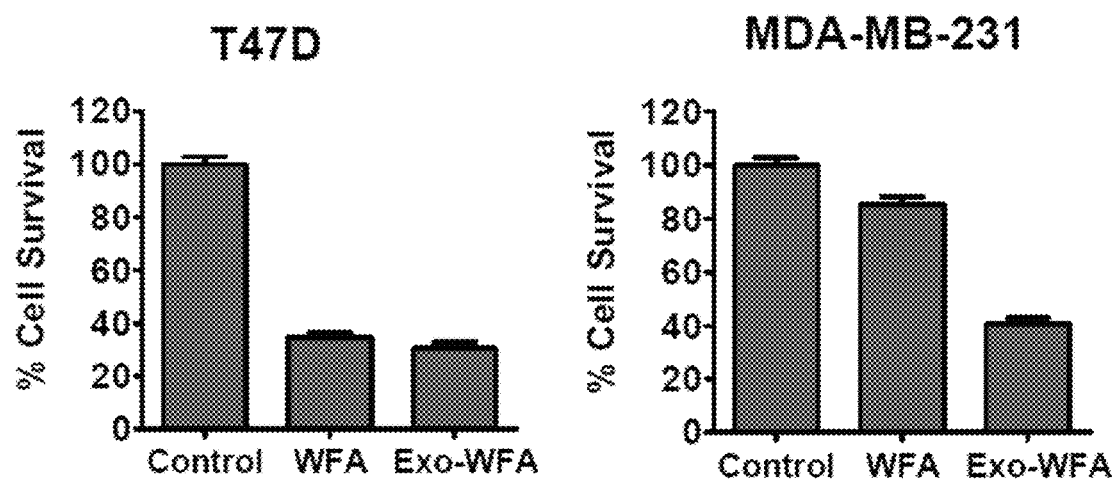
FIG. 20 includes graphs showing the antiproliferative activity of withaferin A-loaded milk exosomes versus free withaferin A (WFA) in human Breast cancer T47D (left graph) and MDA-MB-231 (right graph) cells, where breast cancer cells were treated with WFA (0.6 μM) or WFA loaded milk exosomes (0.6 μM at 45 μg/ml exosomal protein) for 72 hrs.
Figure 21:
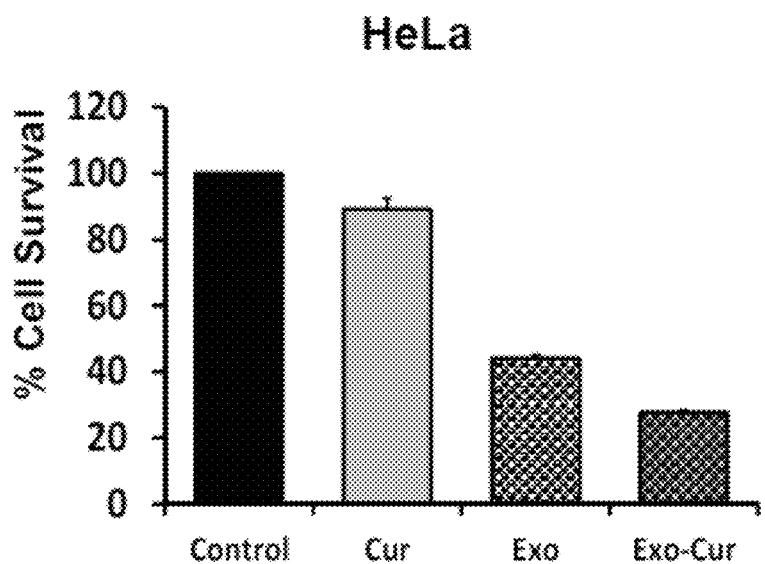
FIG. 21 includes a graph showing the antiproliferative activity of curcumin-loaded milk exosomes versus free curcumin in human uterine cervical cancer (HeLa) cells, where HeLa cells were treated with either 12.5 μM curcumin or 45 μg/ml milk exosomes or curcumin-loaded milk exosomes (12.5 μM curcumin at 45 μg/ml exosomal protein), and where percent cell survival was analyzed by MTT assay.
Figure 22:
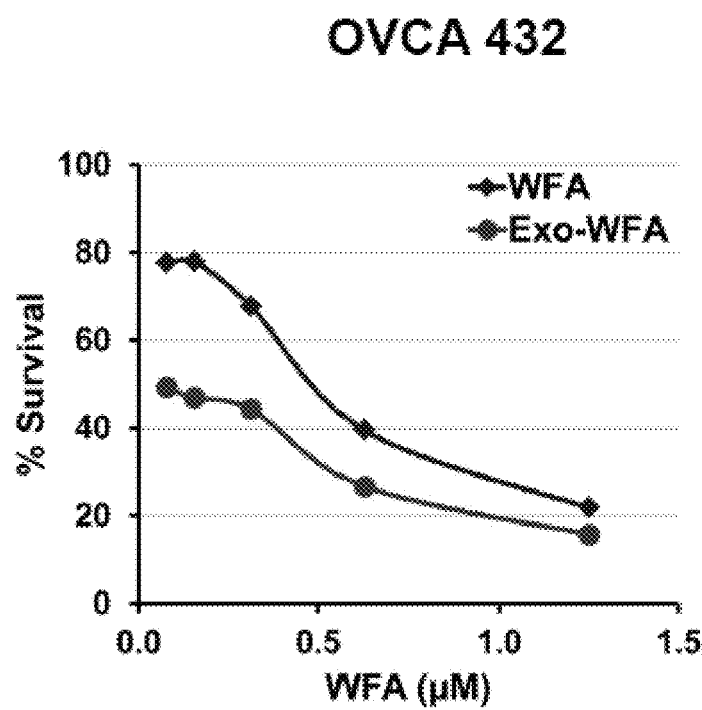
FIG. 22 includes a graph showing the antiproliferative activity of withaferin A-loaded milk exosomes versus free withaferin A in human cisplatin-resistant ovarian cancer OVCA 432 cells, where the withaferin A-loaded milk exosomes and the exosomal protein concentration was maintained constant (50 μg/ml), and where the proliferation were measured by MTT assay.
Figure 23:
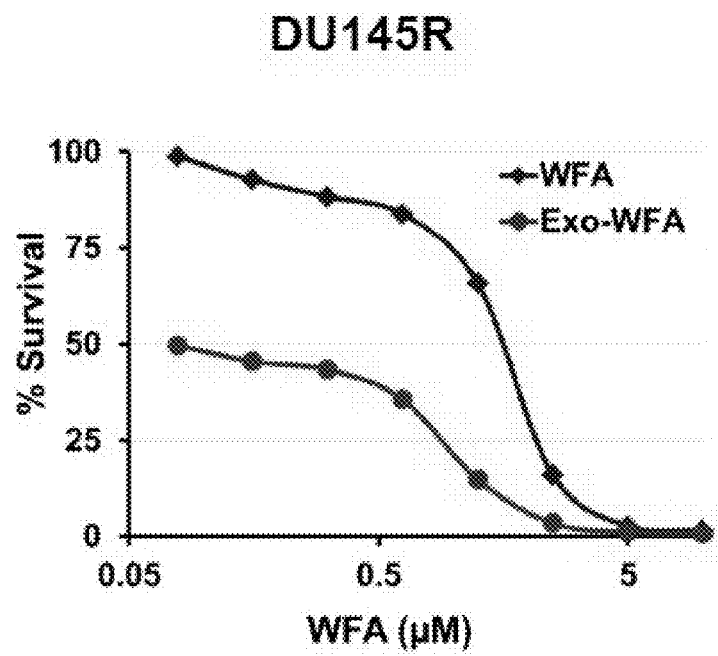
FIG. 23 includes a graph showing the antiproliferative activity of withaferin A-loaded milk exosomes versus free withaferin A in prostate cancer (DU145R) cells that are highly resistant to paclitaxel, where withaferin A-loaded milk exosomes and exosomal protein concentration were maintained constant (50 μg/ml)
Figure 24:
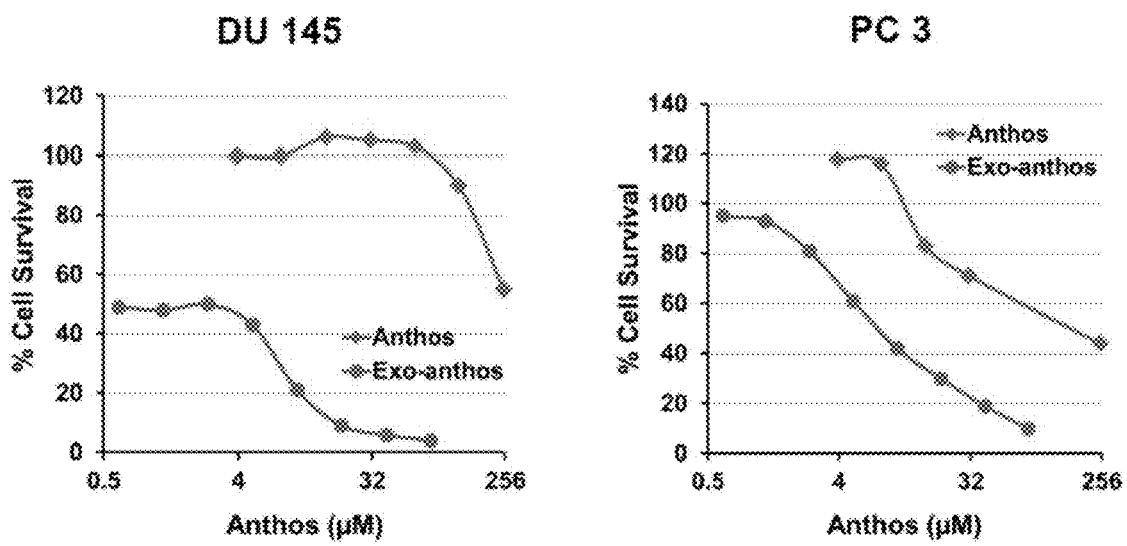
FIG. 24 includes graphs showing the antiproliferative activity of bilberry anthocyanidins-loaded milk exosomes versus free anthocyanidins against prostate DU145 (left graph) and PC3 (right graph) cancer cells, where the bilberry anthocyanidins-loaded milk exosomes and exosomal protein concentration were maintained constant (50 μg/ml)
Figure 25:
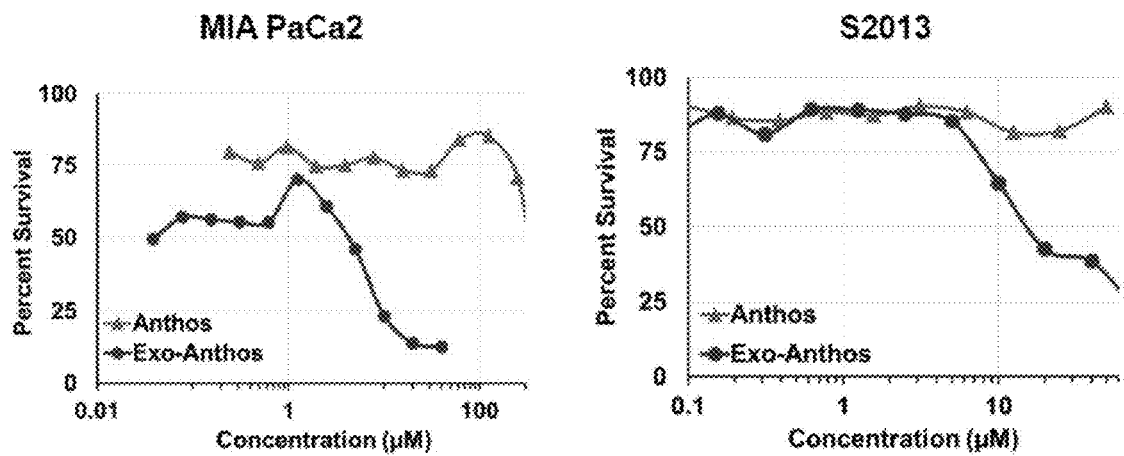
FIG. 25 includes graphs showing the antiproliferative activity of bilberry anthocyanidins-loaded milk exosomes versus free anthocyanidins against pancreatic MIA PaCa2 (left graph) and S2013 (right graph) cancer cells, where the bilberry anthocyanidins-loaded milk exosomes and exosomal protein concentration were maintained constant (50 μg/ml)
Figure 26:
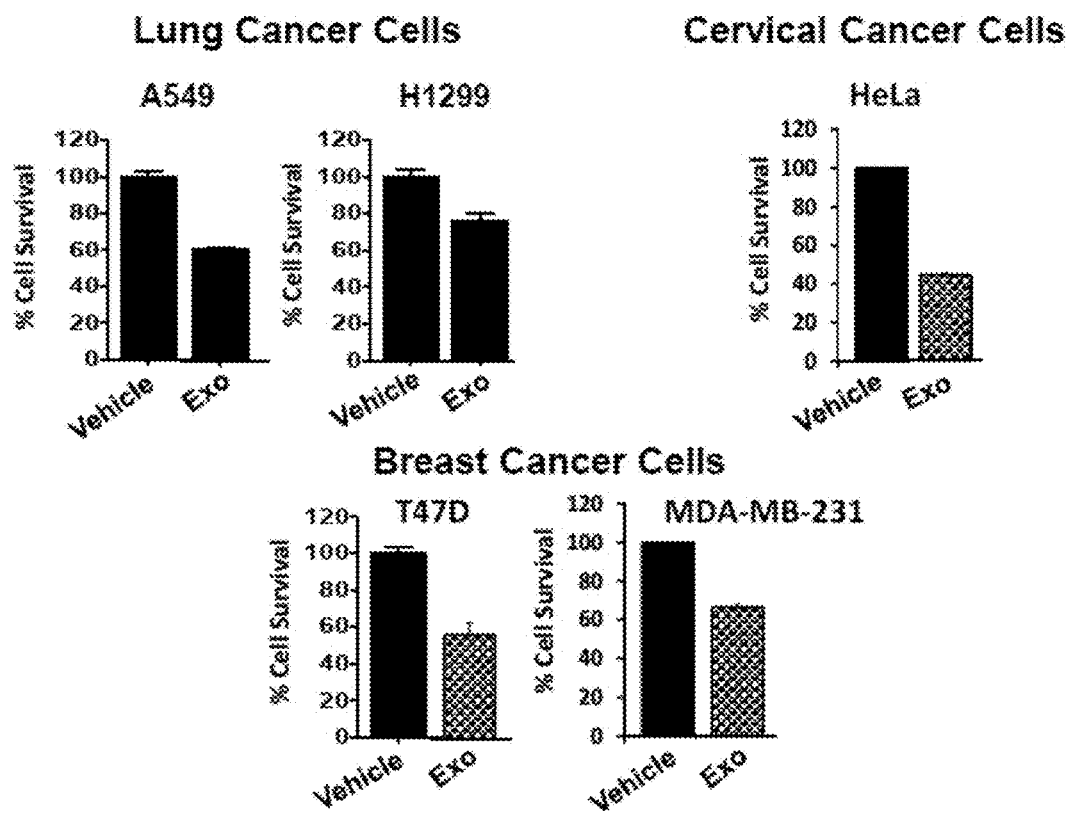
FIG. 26 includes graphs showing the anti-proliferative activity of exosomes per se derived from bovine mature milk in human lung, breast, and uterine cervical cancer cells, where the cancer cells (lung, breast, and cervix) were treated with 50 μg/ml exosomal protein for 72 hrs, and where the percent survival was analyzed by MTT assay.
Figure 27:
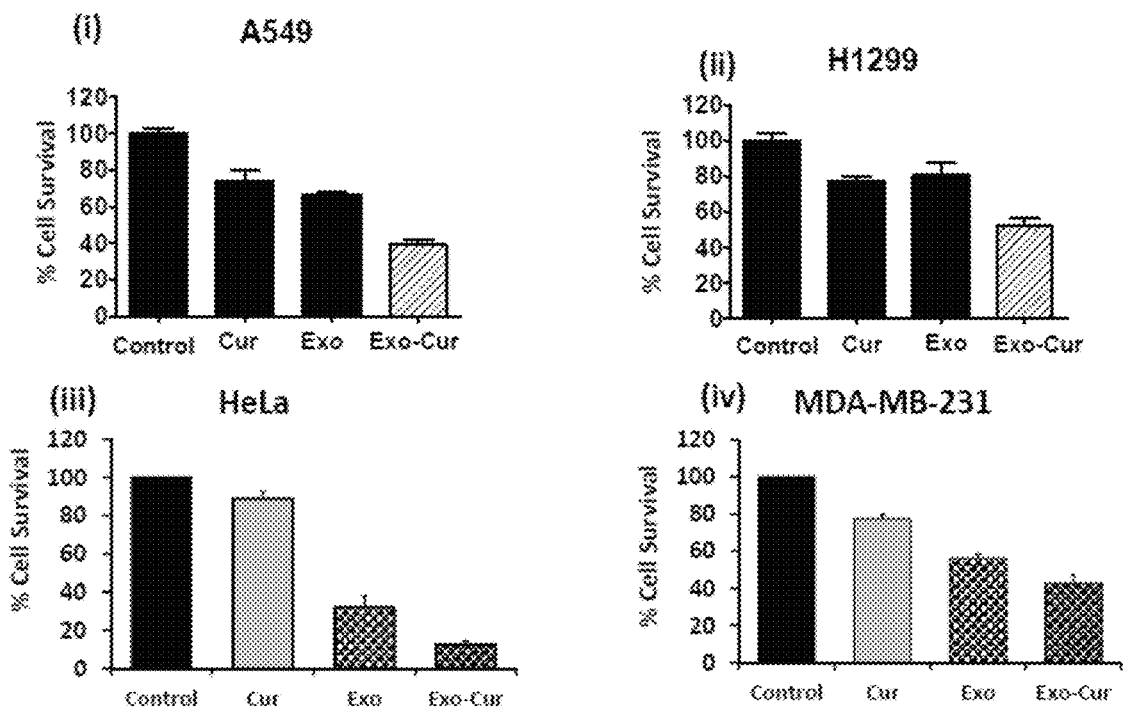
FIG. 27 includes graphs showing the antiproliferative activity of curcumin-loaded colostrum-derived exosomes in human lung, breast, and uterine cervical cancer cells, where lung A549 and H1299 cancer cells were treated with curcumin (1.56 exosomal protein (1.56 μg/ml), or curcumin-loaded milk exosomes (1.56 μM at 3.12 μg/ml exosomal protein) for 72 hrs, and where the cervical HeLa cancer cells and breast MDA-MB-231 cancer cells were treated with either 12.5 μM curcumin or 45 μg/ml milk exosomes or curcumin-loaded bovine colostrum exosomes (12.5 μM curcumin at 45 μg/ml exosomal protein)

Example 4—Effect of Therapeutic Agent-Loaded Milk- and Colostrum-Derived Exosomes on the Growth of Human Cancer Cells Anti-proliferative effects of curcumin-, bilberry anthocyanidins-, or withaferin A-loaded milk exosomes were tested against lung, breast, cervical, ovarian, prostate, and pancreatic cancer cells. In particular, dose-response curves were generated to assess the anti-proliferative effect of curcumin-loaded milk exosomes on human lung cancer A549 and H1299 cells (FIG. 16) bilberry anthocyanidins-loaded milk exosomes on human lung cancer A549 and H1299 cells (FIG. 17), withaferin A-loaded milk exosomes on human lung cancer A549 and H1299 cells (FIG. 18), curcumin-loaded milk exosomes on human breast cancer T47D and MDA-MB-231 cells (FIG. 19), withaferin A-loaded milk exosomes on human breast cancer T47D and MDA-MB-231 cells (FIG. 20), curcumin-loaded milk exosomes in human uterine cervical cancer (HeLa) cells (FIG. 21), withaferin A-loaded milk exosomes on cisplatin-resistant ovarian cancer OVCA 432 cells (FIG. 22), withaferin A-loaded milk exosomes on paclitaxel-resistant prostate cancer DU145R cells (FIG. 23), bilberry anthocyanidins-loaded milk exosomes on prostate DU145 and PC3 cancer cells (FIG. 24), and bilberry anthocyanidins-loaded milk exosomes on pancreatic MIA PaCa2 and S2013 cancer cells (FIG. 25). Upon analysis of the results, it was observed that the therapeutic agent-loaded milk exosomes exhibited significantly higher anti-proliferative activity when compared to the effect of the free therapeutic agents on the cancer cells tested, with the activity being more prominent at lower drug concentrations. Additionally, it was observed that colostrum-derived exosomes loaded with therapeutic agent had similar effects in human lung, breast, and uterine cervical cancer cells (FIG. 27). Greater anti-proliferative activity was observed when exosomal concentration was kept constant and the therapeutic agent concentration varied, implying some intrinsic protective effects of the exosomes. Unexpectedly, exosomes from both milk and colostrum alone showed potent inhibition of lung, cervical, and breast cancer cell growth, indicating the presence of cancer-killing factors (e.g., miRNAs) in those particles (FIG. 26).

Example 5—Biodistribution of Exosomes

Figure 28:
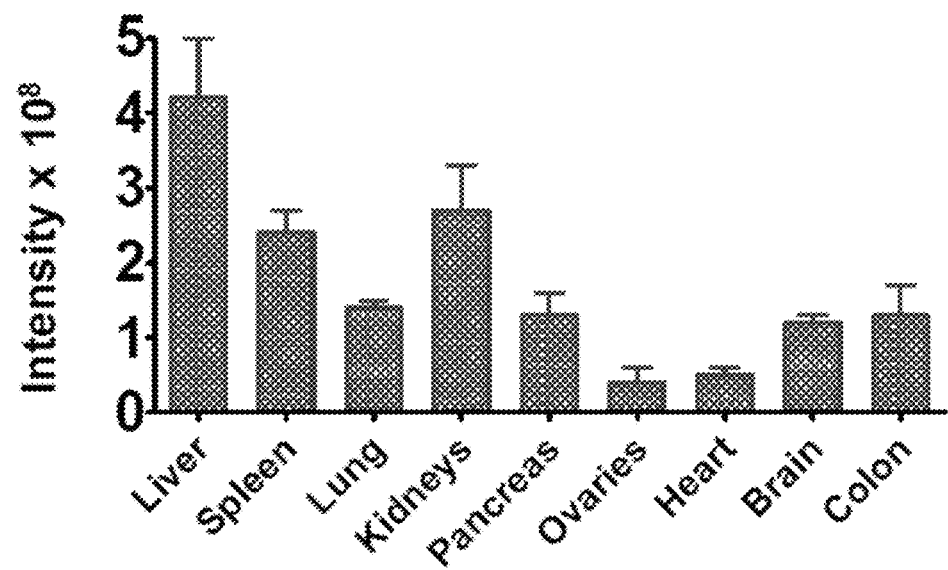
FIG. 28 includes a graph showing the biodistribution of DiR-labeled exosomes administered by oral gavage in nude mice, where different organs collected at euthanasia after 4 days of treatment were imaged on Photon Imager Optima (Biospace lab) and relative intensity was measured.
Figure 29:
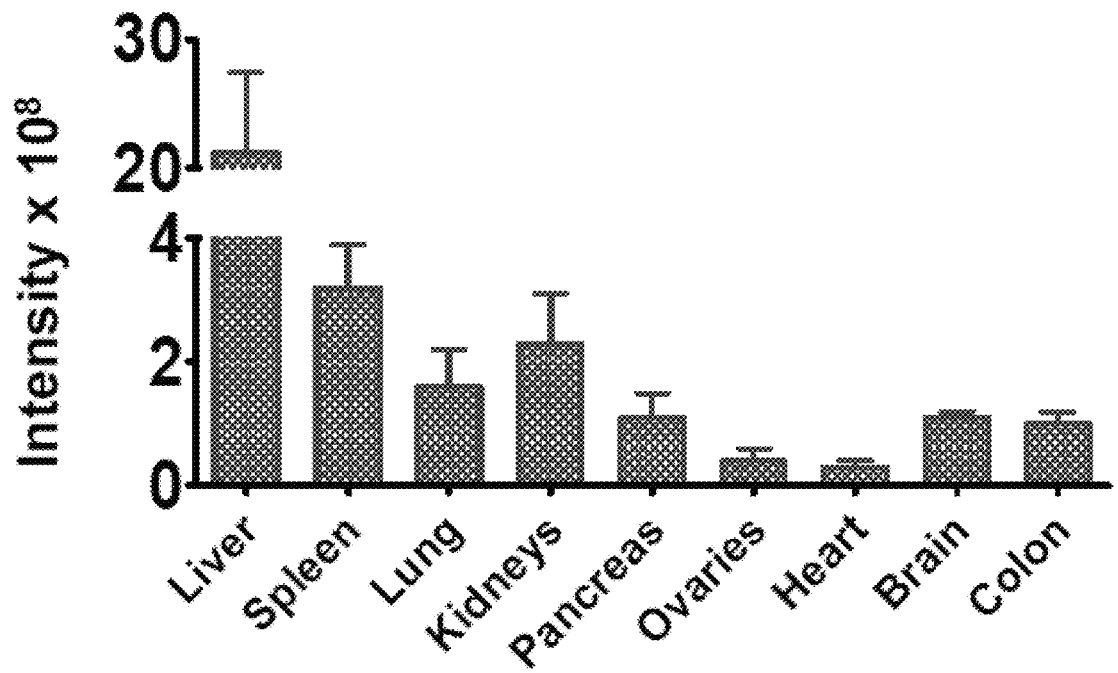
FIG. 29 includes a graphs showing the biodistribution of DiR-labeled exosomes administered intravenously in nude mice, where different organs collected at euthanasia after 4 days of treatment were imaged on Photon Imager Optima (Biospace lab) and relative intensity was measured.
Figure 30:
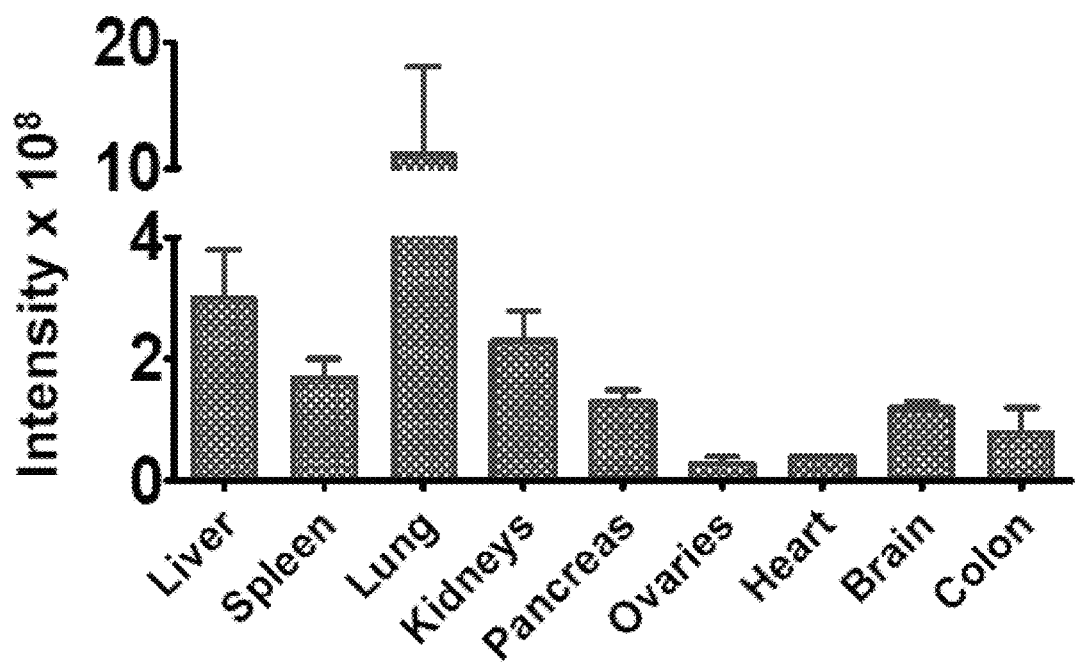
FIG. 30 includes a graph showing the biodistribution of DiR-labeled milk exosomes administered via intranasal route in nude mice, where different organs collected at euthanasia after 4 days of treatment were imaged on Photon Imager Optima (Biospace) and relative intensity was measured.
Figure 31:
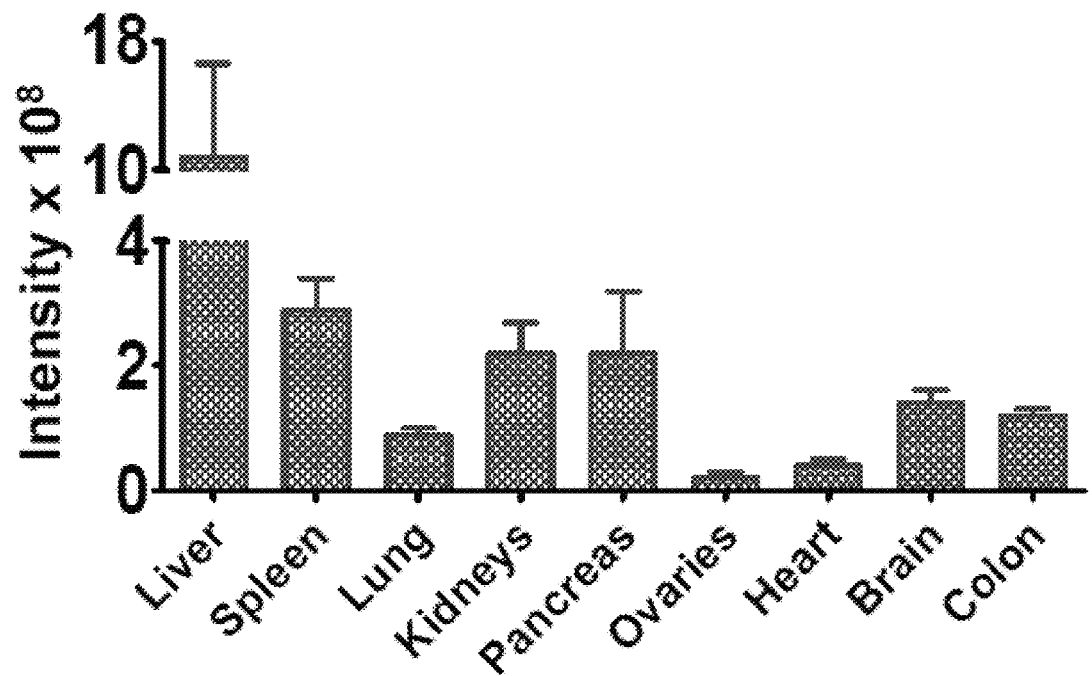
FIG. 31 includes a graph showing the biodistribution of DiR-labeled exosomes administered by intraperitoneal route in nude mice, where different organs collected at euthanasia after 4 days of treatment were imaged on Photon Imager Optima (Biospace lab) and relative intensity was measured.

To examine the biodistribution of milk-derived exosomes in whole animals, evidence of uptake and tissue distribution was obtained by labeling milk exosomes with a near-IR fluorescent label, DiR (Life Technologies, Carlsbad, Calif.), and treating female nude mice with a single dose of the exosomes administered by oral gavage, intravenously, intranasally, or intraperitoneally (2 mg Exo protein/mouse). Imaging (Biospace lab Photon Imager Optima) of the live animals showed a strong fluorescent signal, with the signal being detected even after 4 d. Harvesting of various organs following euthanasia and imaging showed that the oral gavage (FIG. 28), intravenous (FIG. 29), intranasal (FIG. 30), and intraperitoneal (FIG. 31) routes resulted in similar tissue distribution of the exosomes, with the exceptions that, with intravenous and intraperitoneal administration, the liver was the predominant site of distribution, and that, when intransal administration was used, the lung was the predominant site. These data indicate that various routes of administration could be utilized effectively for the delivery of the exosomes and for the selection of target organs.

Figure 32:
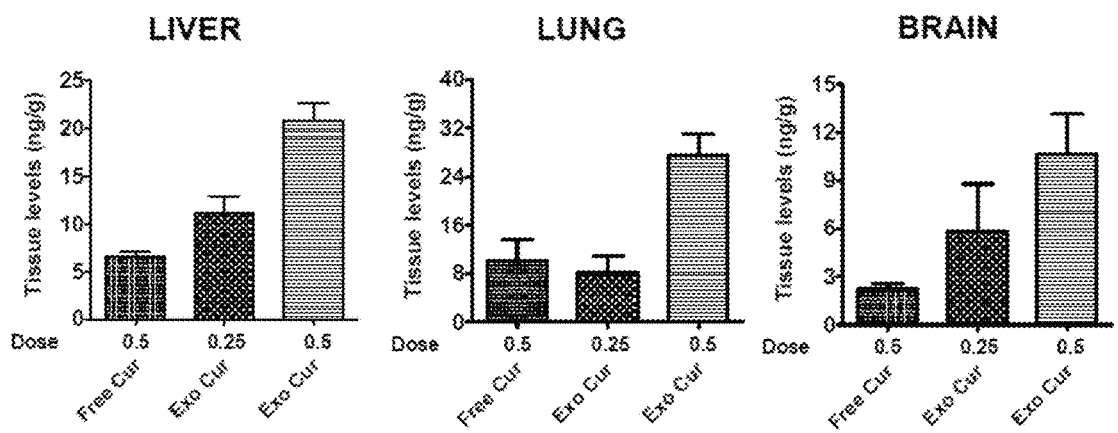
FIG. 32 includes graphs showing tissue distribution of curcumin in rats treated with exosomal curcumin or free curcumin, where curcumin levels were assessed in liver, lung, and brain tissues of female Sprague Dawley rats treated with either free curcumin (0.5 mg/rat/day) or exosomal-curcumin (0.25 and 0.5 mg/rat/day) by oral gavage for 14 days.

Example 6—Tissues Therapeutic Agent Levels Following Administration of Therapeutic Agent-Loaded Milk Exosomes To determine drug distribution delivered via the milk exosomes, female Sprague Dawley rats (7 to 8 weeks old) were treated on alternate days by gavage with milk exosomes loaded with curcumin as a model compound (25 mg Exo protein/kg/dose; drug load 10%), or equivalent amount of free curcumin. Two weeks later animals were euthanized and curcumin levels were measured by solvent extraction and UPLC. Data showed 3-5 times higher levels in the lung, liver and brain with the exosomal formulation compared with free curcumin (FIG. 32). The higher brain curcumin levels with exosomal formulation can be either due to sheltering of curcumin within exosomes, thus minimizing its metabolism, or that the exosomal formulation crossed the blood brain barrier more readily compared to free curcumin, or both. The higher levels of curcumin in the liver and lung are more likely to be due to its curtailed metabolism.

Example 7—Toxicity of Therapeutic Agent-Loaded Milk Exosomes

To determine potential acute toxicities associated with milk-derived exosomes, female Sprague Dawley rats were treated with bovine milk-derived exosomes (5 mg/rat) or vehicle (PBS) intraperitoneally and blood was analyzed for any systemic toxicity 1 hr, 3 hrs, and 6 hrs following administration using an automated AU640® Chemistry Analyzer (Beckman Coulter, Inc., Brea, Calif.) or a Cell-Dyn 3500 hematology analyzer by Antech diagnostics (Abbott Laboratories, Santa Clara, Calif.). Upon comparison with the vehicle treatment, the experimental group showed no significant alterations in the liver and kidney function enzymes (Table VI) or serum proteins (Table VII), as well as no significant alterations in hematopoietic parameters (Table VIII). These data coupled with lack of inflammatory response (see below) indicated that the milk-derived exosomes at the given dose were well tolerated.

TABLE VI

Effect on liver enzymes and kidney functions (systemic toxicity) following acute exposure to milk-derived exosomes.

| | Milk-exosomes (5 mg/rat) | | | |
|---|---|---|---|---|
| Biochemical profile | Control | 1 h | 3 h | 6 h |
| AST (SGOT) | 202.8 ± 49.3 | 168.3 ± 36.1 | 264.3 ± 61.6 | 204.8 ± 43.1 |
| ALT (SGPT) | 65.3 ± 12.8 | 56.3 ± 8.7 | 61.3 ± 6.8 | 56.8 ± 13.4 |
| Alk Phosphatase | 192 ± 18.3 | 151.0 ± 17.4 | 187.5 ± 50.5 | 162.3 ± 23.8 |
| GGT | 1.3 ± 0.5 | 3.8 ± 2.2 | 2.3 ± 1.3 | 2.8 ± 2.1 |
| Amylase | 529.5 ± 107.2 | 413.5 ± 47.9 | 423.5 ± 40.1 | 585.5 ± 162 |
| CPK | 873.5 ± 238.6 | 685.5 ± 175.1 | 1329.0 ± 394.8 | 915.8 ± 388 |
| BUN | 19.8 ± 0.5 | 19.8 ± 2.8 | 18.8 ± 2.2 | 17.5 ± 2.6 |
| BUN/Creatinine Ratio | 36 ± 3.6 | 44.0 ± 1.8 | 47.5 ± 4.9 | 33.5 ± 5.0 |
| Phosphorus | 18.4 ± 3.0 | 13.5 ± 1.2 | 13.9 ± 1.1 | 13.1 ± 0.9 |
| Calcium | 12.4 ± 1.0 | 11.9 ± 0.8 | 12.4 ± 0.5 | 11.7 ± 0.9 |

TABLE VII

Effect on serum proteins and other molecules (systemic toxicity) following acute exposure to milk-derived exosomes.

| | Milk-exosomes (5 mg/rat) | | | |
|---|---|---|---|---|
| Biochemical profile | Control | 1 h | 3 h | 6 h |
| Total Protein | 6.9 ± 0.4 | 6.4 ± 0.2 | 6.4 ± 0.3 | 6.5 ± 0.5 |
| Albumin | 3.8 ± 0.2 | 3.7 ± 0.2 | 3.6 ± 0.2 | 3.7 ± 0.3 |
| Globulin | 3.1 ± 0.2 | 2.8 ± 0.1 | 2.8 ± 0.2 | 2.8 ± 0.2 |
| A/G Ratio | 1.2 ± 0.1 | 1.3 ± 0.0 | 1.3 ± 0.1 | 1.3 ± 0.0 |
| Glucose | 193.8 ± 55.8 | 158.0 ± 13.0 | 186.5 ± 42.2 | 208.3 ± 28.6 |
| Cholesterol | 94 ± 10.1 | 101.3 ± 9.5 | 85.8 ± 15.8 | 81.5 ± 9.3 |
| Triglyceride | 134.5 ± 26.6 | 69.0 ± 18.4 | 79.8 ± 16.7 | 86.0 ± 26.8 |

TABLE VIII

Effect on the hematological parameters (systemic toxicity) following acute exposure to milk-derived exosomes.

| | Milk-exosomes (5 mg/rat) | | | |
|---|---|---|---|---|
| Biochemical profile | Control | 1 h | 3 h | 6 h |
| WBC | 5.7 ± 2.5 | 6.8 ± 1.0 | 5.7 ± 1.0 | 6.5 ± 1.6 |
| HGB | 14.0 ± 1.2 | 11.2 ± 4.7 | 13.2 ± 0.6 | 13.5 ± 0.9 |
| HCT | 44.0 ± 3.5 | 42.3 ± 3.9 | 41.3 ± 1.9 | 41.5 ± 3.4 |
| MCV | 60.8 ± 1.0 | 61.0 ± 1.2 | 61.5 ± 1.0 | 59.0 ± 1.8 |
| MCHC | 31.8 ± 0.5 | 26.4 ± 10.6 | 32.0 ± 0.9 | 32.4 ± 1.0 |
| Platelet Count | 689.0 ± 145.8 | 850.0 ± 8.5 | 465.0 ± 296.0 | 605.8 ± 433.2 |
| Neutrophils | 12.0 ± 3.5 | 15.0 ± 2.8 | 39.3 ± 27.4 | 32.7 ± 35.8 |
| Lymphocytes | 84.5 ± 4.5 | 48.5 ± 37.6 | 41.5 ± 36.0 | 50.8 ± 40.4 |
| Absolute Neutrophils | 637.3 ± 136.6 | 495.8 ± 572.7 | 1702.0 ± 1672.8 | 1456.0 ± 1747.6 |
| Absolute Lymphocytes | 4886.5 ± 2252.6 | 3277.8 ± 2677.6 | 2453.5 ± 2308.1 | 3703.3 ± 3357.8 |
| Absolute Monocytes | 102.6 ± 83.6 | 2816.8 ± 3165.1 | 1036.0 ± 1875.0 | 960.3 ± 1657.2 |
| Absolute Eosinophils | 75.3 ± 29.8 | 135.5 ± 20.6 | 107.5 ± 51.3 | 86.8 ± 72.8 |

Similar experiments were performed to assess toxicity following chronic exposure to colostrum-derived and milk-derived exosomes and to determine whether differences in toxicity following the administration of milk-derived versus colostrum-derived exosomes. In those experiments, female Sprague-Dawley rats (6-7 weeks old) were provided with control diet (AIN 93M) or water ad libitum, and were treated with milk- and colostrum-derived exosomes (5 mg/rat) by oral gavage daily for 15 days. At euthanasia, blood was collected and again analyzed using an automated AU640® Chemistry Analyzer (Beckman Coulter, Inc., Brea, Calif., USA) or a Cell-Dyn 3500 hematology analyzer by Antech diagnostics (Abbott laboratories, Santa Clara, Calif., USA). Following comparison with the vehicle treatment, neither experimental group showed significant alterations in the liver and kidney function enzymes (Table IX) or serum proteins (Table X), and further showed no significant alterations in hematopoietic parameters (Table XI). Additionally, no significant differences were observed between the group administered milk-derived exosomes and the group administered colostrum-derived exosomes.

TABLE IX

Effect on liver enzymes and kidney functions (Systemic toxicity) following chronic exposure to milk- and colostrum-derived exosomes.

|  | | Exosomes (5 mg/animal) daily | |
|---|---|---|---|
| Biochemical test | Control | Milk | Colostrum |
| AST (SGOT) | 235 ± 85.7 | 220.5 ± 58.7 | 223.5 ± 62.8 |
| ALT (SGPT) | 66.0 ± 3.2 | 64.2 ± 9.7 | 65.5 ± 5.5 |
| Alk Phosphatase | 243.8 ± 58.9 | 151.8 ± 55.7 | 183.8 ± 42.8 |
| GGT | 5.3 ± 1.0 | 3.3 ± 1.7 | 3.5 ± 0.6 |
| Amylase | 529.8 ± 55.3 | 496.0 ± 42.9 | 588.5 ± 123.3 |
| CPK | 25.0 ± 0.0 | 25.0 ± 0.0 | 25.0 ± 0.0 |
| BUN | 23.8 ± 3.1 | 18.8 ± 1.9 | 22.0 ± 3.7 |
| BUN/Creatinine Ratio | 98.8 ± 42.1 | 65.5 ± 30.3 | 78.8 ± 34.2 |
| Phosphorus | 15.9 ± 1.7 | 15.1 ± 2.4 | 15.0 ± 2.5 |
| Calcium | 10.6 ± 1.1 | 11.1 ± 1.1 | 10.8 ± 1.3 |

TABLE X

Effect on serum proteins and other molecules (Systemic toxicity) following chronic exposure to milk- and colostrum-derived exosomes.

|  | | Exosomes (5 mg/animal) daily | |
|---|---|---|---|
| Biochemical test | Control | Milk | Colostrum |
| Total Protein | 6.8 ± 0.2 | 6.7 ± 0.5 | 6.7 ± 0.4 |
| Albumin | 3.9 ± 0.2 | 4.0 ± 0.3 | 3.9 ± 0.3 |
| Globulin | 2.9 ± 0.1 | 2.7 ± 0.2 | 2.8 ± 0.4 |
| A/G Ratio | 1.3 ± 0.1 | 1.5 ± 0.1 | 1.5 ± 0.2 |
| Glucose | 205.5 ± 31.0 | 193.5 ± 34.8 | 183.3 ± 21.1 |
| Cholesterol | 105.8 ± 14.6 | 105.5 ± 12.9 | 96.5 ± 10.2 |
| Triglyceride | 117.3 ± 9.4 | 69.3 ± 13.8 | 59.0 ± 24.2 |

TABLE XI

Effect on the hematological parameters (Systemic toxicity) following chronic exposure to milk-derived exosomes.

|  | | Exosomes (5 mg/animal) daily | |
|---|---|---|---|
| Biochemical test | Control | Milk | Colostrum |
| WBC | 5.7 ± 1.7 | 7.0 ± 2.0 | 6.8 ± 1.7 |
| HGB | 14.0 ± 0.3 | 13.8 ± 0.6 | 13.8 ± 1.1 |
| HCT | 43.3 ± 2.1 | 42.3 ± 1.9 | 42.7 ± 3.8 |
| MCV | 45.5 ± 29.0 | 59.3 ± 1.7 | 58.7 ± 2.1 |
| MCHC | 32.3 ± 2.3 | 32.8 ± 0.5 | 32.3 ± 0.6 |
| Platelet Count | 755.7 ± 134.9 | 772.8 ± 85.8 | 883.3 ± 266.0 |
| Neutrophils | 11.5 ± 3.0 | 13.5 ± 8.4 | 15.3 ± 3.6 |
| Lymphocytes | 86.0 ± 2.8 | 81.0 ± 7.4 | 80.8 ± 2.2 |
| Absolute Neutrophils | 668.5 ± 324.6 | 883.0 ± 422.2 | 995.8 ± 196.9 |
| Absolute Lymphocytes | 4852.0 ± 1413.4 | 5701.5 ± 1881.1 | 5469.8 ± 1472.6 |
| Absolute Monocytes | 61.8 ± 46.2 | 212.5 ± 115.9 | 204.0 ± 104.4 |
| Absolute Eosinophils | 67.8 ± 55.5 | 178.0 ± 94.6 | 80.5 ± 93.8 |

Figure 33:
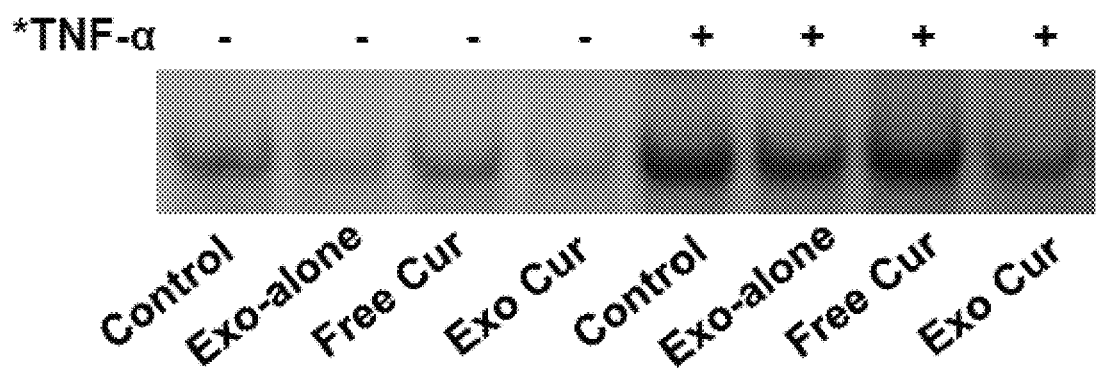
FIG. 33 includes an image showing inhibition of constitutive and TNF-α induced activation of the inflammation marker NF-κB by free curcumin (25 μM) and curcumin-loaded bovine colostrum exosomes (25 μM curcumin; 90 μg/ml exo protein), where human lung A549 cancer cells were pre-treated with exosomes (Exo), curcumin (Cur) or curcumin-loaded exosomes (Exo-cur) for 6 hrs followed by treatment with or without tumor necrosis factor-alpha (TNF-α) (10 ng/ml) to induce NF-κB activation, and where NF-κB levels were determined by electrophoretic mobility shift assay (EMSA).
Figure 34:
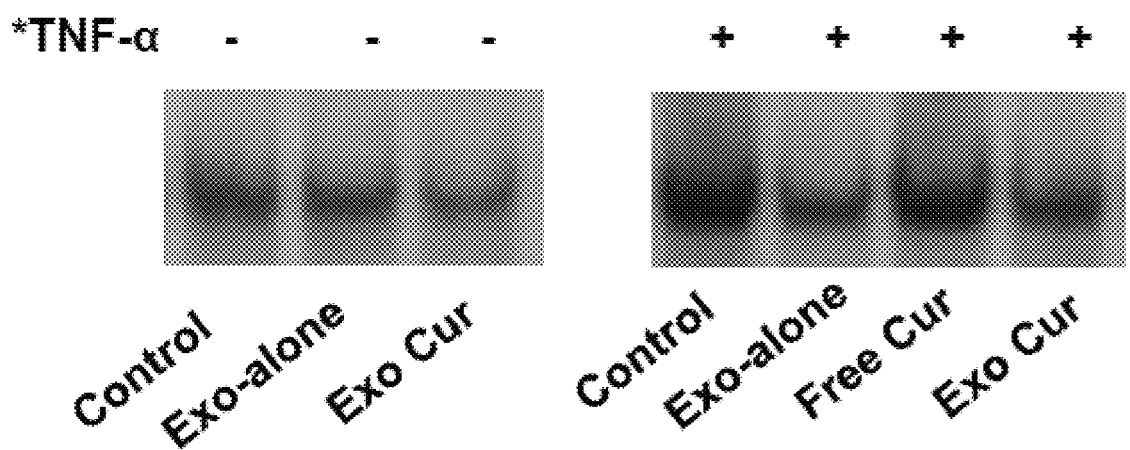
FIG. 34 includes images showing the inhibition of constitutive and TNF-α induced activation of the inflammation marker NF-κB by free curcumin (25 μM) and curcumin-loaded bovine colostrum exosomes (25 μM curcumin; 90 μg/ml Exo protein), where human lung H1299 cancer cells were pre-treated with exosomes (Exo), curcumin (Cur) or curcumin-loaded exosomes (Exo-cur) for 6 hrs followed by treatment with or TNF-α (10 ng/ml) to induce NF-κB activation, and where NF-κB levels were determined by EMSA.
Figure 35:
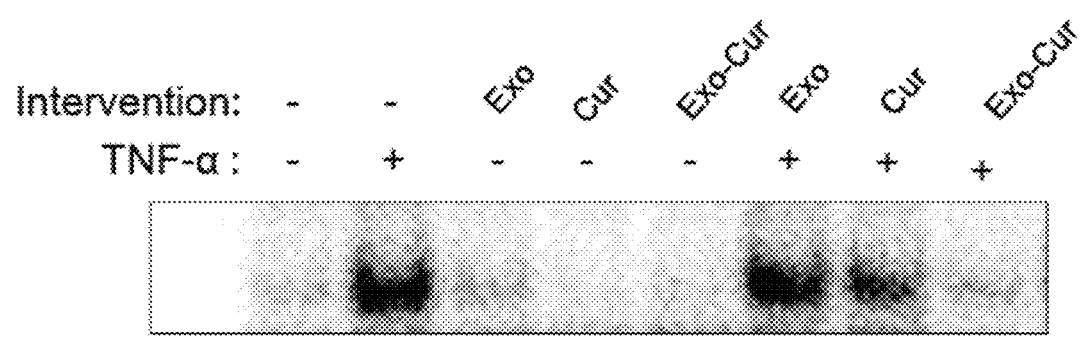
FIG. 35 includes an image showing inhibition of activation of the inflammation marker NF-κB by free curcumin (25 μM) and curcumin-loaded bovine colostrum-derived exosomes (25 μM curcumin; 90 μg/ml Exo protein), where human breast MDA-MB-231 cancer cells were pre-treated with exosomes (Exo), curcumin (Cur) or curcumin-loaded exosomes (Exo-cur) for 6 hrs followed by treatment with or without TNF-α (10 ng/ml) to induce NF-κB activation, and where NF-κB levels were determined by EMSA.
Figure 36:
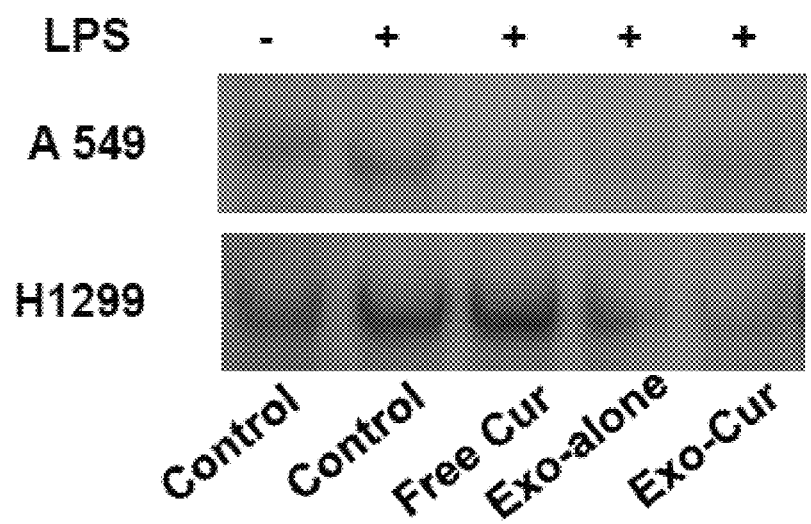
FIG. 36 includes images showing the inhibition of the lipopolysaccharide (LPS)-induced activation of the inflammation marker NF-κB by free curcumin (25 μM) and curcumin-loaded bovine colostrum exosomes (25 μM curcumin; 90 μg/ml Exo protein), where human lung (A549 and H1299) cancer cells were pre-treated with exosomes (Exo), curcumin (Cur) or curcumin-loaded exosomes (Exo-cur) for 6 hrs followed by treatment with LPS (1 μg/ml) to induce NF-κB activation, and where NF-κB levels were determined by EMSA.

Example 8—Effect of Therapeutic Agent-Loaded Milk- and Colostrum-Derived Exosomes on Inflammatory Markers To assess the effect of therapeutic agent-loaded milk- and colostrum-derived exosomes on inflammatory markers, human lung A549 cancer cells were initially pre-treated with colostrum-derived exosomes (Exo), curcumin (Cur) or curcumin-loaded colostrum-derived exosomes (Exo-cur) for 6 hrs followed by treatment with or without tumor necrosis factor (TNF-α) (10 ng/ml) to induce NF-κB activation, and NF-κB levels were subsequently determined by electrophoretic mobility shift assay (EMSA). Both the colostrum-derived exosomes alone and the curcumin-loaded colostrum-derived exosomes showed anti-inflammatory activity against constitutive and TNF-α induced inflammation (FIG. 33). Colostrum-derived exosomes alone and curcumin-loaded colostrum-derived exosomes also each exhibited anti-inflammatory activity against constitutive and TNF-α induced inflammation in human lung H1299 cancer cells (FIG. 34) and in human breast MDA-MB-231 cancer cells (FIG. 35) when those cells were pre-treated with exosomes (Exo), curcumin (Cur) or curcumin-loaded exosomes (Exo-cur) for 6 hrs followed by treatment with or without tumor necrosis factor TNF-α (10 ng/ml) to induce NF-κB activation. Colostrum-derived exosomes alone and curcumin-loaded colostrum-derived exosome also showed modest protection against lipopolysaccharide (LPS)-induced NF-κB activation in lung A549 and H1299 cancer cells (FIG. 36).

Example 9—Milk- and Colostrum-Derived Exosome Markers

Figure 37:
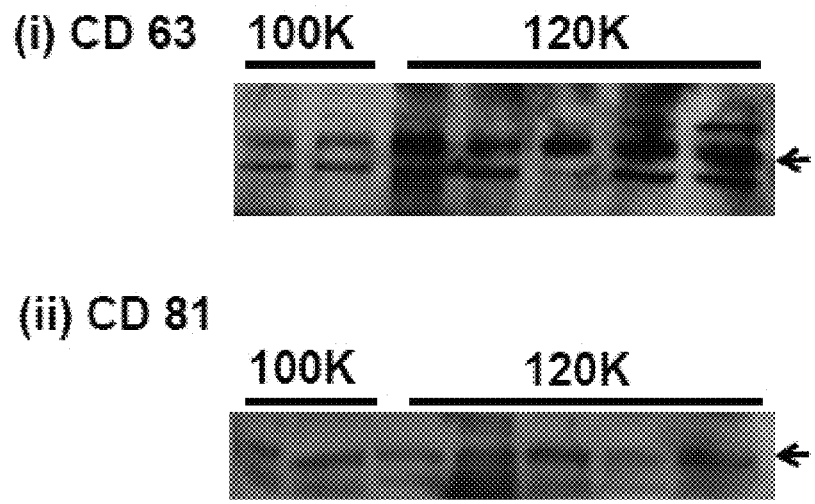
FIG. 37 includes images showing milk-derived exosome surface markers, where milk-derived exosomes isolated by ultracentrifugation were analyzed for exosomal surface markers CD63 and CD81 by western blot analysis.
Figure 38:
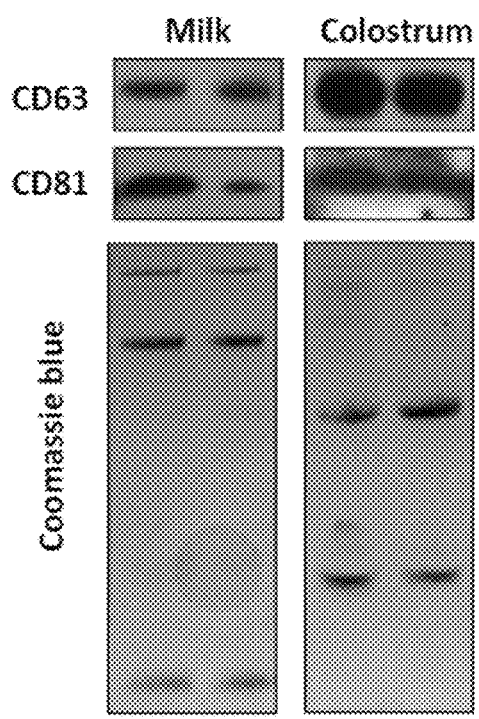
FIG. 38 includes images showing exosome-related surface markers, where milk- and colostrum-derived exosomes were analyzed for exosomal surface markers (transpanins) CD63 and CD81 by western blot analysis.
Figure 39:
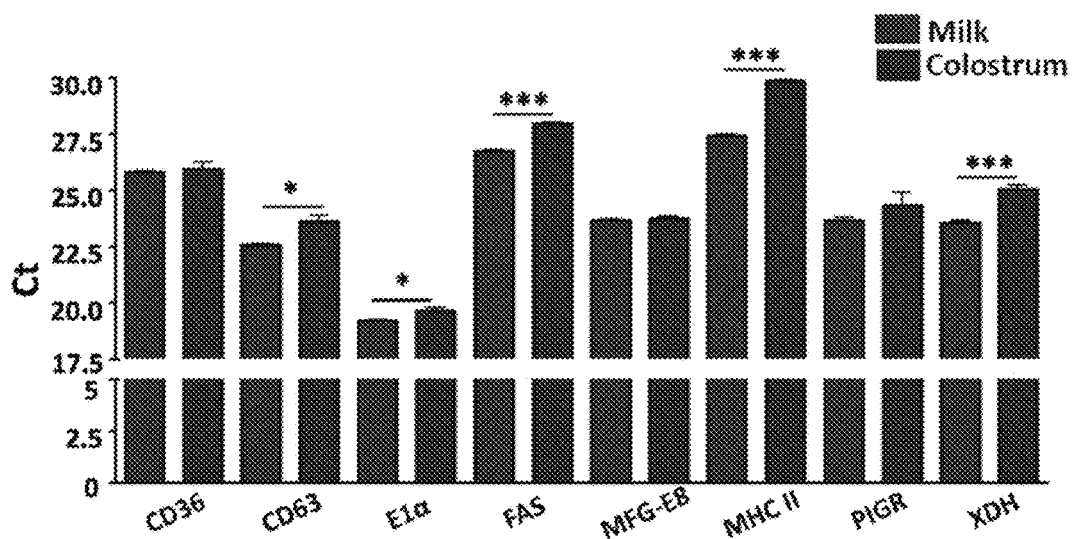
FIG. 39 includes a graphs showing exosome-related mRNA expression, where bovine milk- and colostrum-derived exosomes were analyzed for 8 exosome-related mRNAs by RT-PCR.
Figure 40:
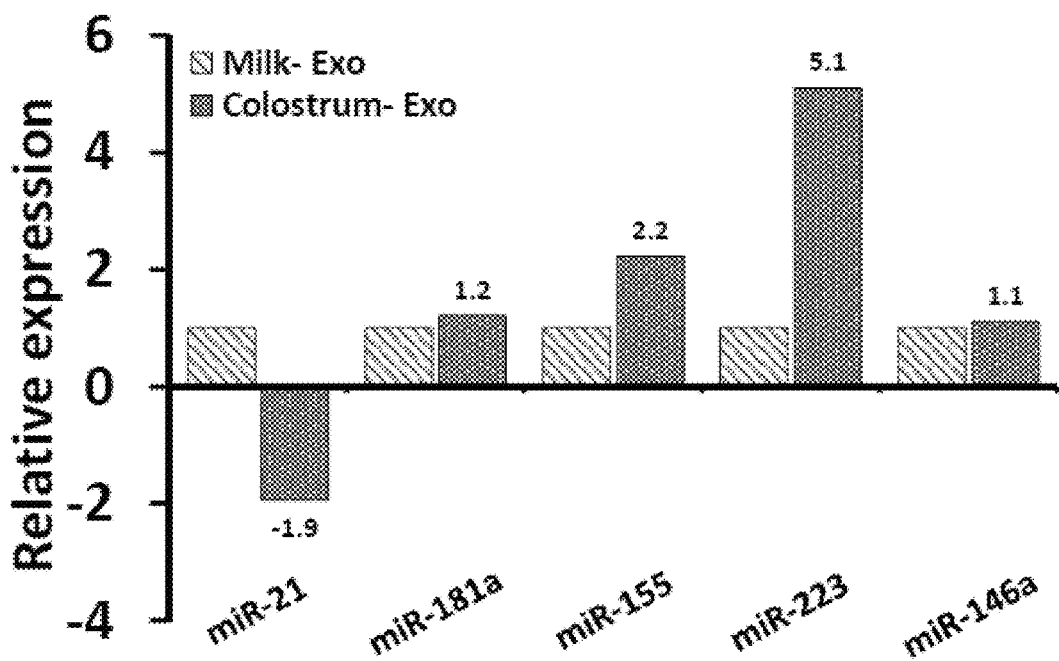
FIG. 40 includes a graph showing that milk- and colostrum-derived exosomes carry immune related miRNAs, where bovine milk- and colostrum-derived exosomes were analyzed for five immune-related miRNAs by RT-PCR.

Milk- and colostrum-derived exosomes were analyzed for transmembrane protein markers or transpanins (e.g., CD63 and CD81) by western blot analysis. Results from those experiments confirmed that the milk- and colostrum-derived exosomes carried those surface proteins, with substantially higher levels of CD63 in colostrum exosomes (FIGS. 37 and 38). The presence of select exosomal proteins in both milk- and colostrum-derived exosomes was also analyzed by RT-PCR (FIG. 39), which confirmed that the microvesicles isolated from milk and colostrum were indeed exosomes. Of the eight immune function-related proteins analyzed, RNA levels showed that 5 proteins were significantly higher in colostrum versus milk-derived exosomes suggesting that colostrum-derived exosomes can, in some instances, serve as a more effective immune booster. Additionally, the presence of immune related miRNAs in colostrum- and milk-derived exosomes was confirmed by RT-PCR (FIG. 40). Two miRNAs namely, miR-155 and miR-223 were significantly higher in colostrum compared to milk-derived exosomes.

Example 10—Acute Immunological Response with Milk Exosomes

Figure 41:
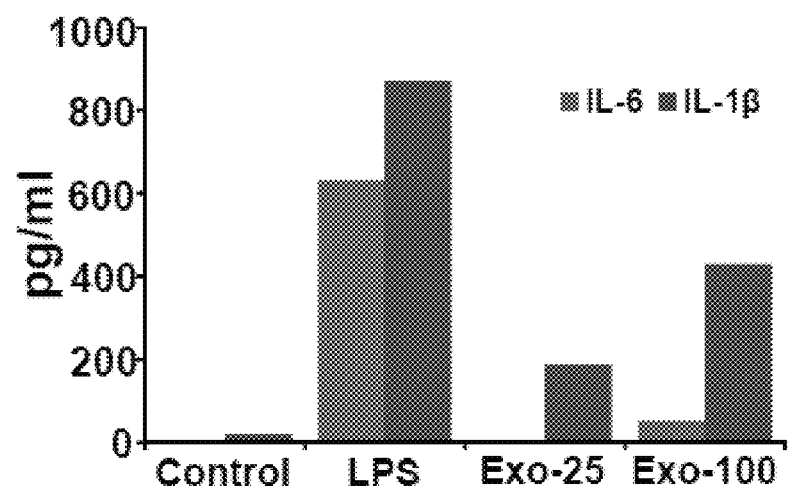
FIG. 41 includes a graph showing the immune response in macrophages after 6 hrs of treatment with lipopolysaccharide (LPS) (100 ng/ml) or milk-derived exosomes (Exo-25=25 μs and Exo-100=100 μg Exo protein/ml) in cell culture.

To test early immunological response of milk exosomes in vitro, THP-1 monocytes were differentiated into macrophages with 100 nM phorbol 12-myristate 13-acetate and then treated with milk exosomes at 25 and 100 µg/ml or LPS (100 ng/ml) for 1, 3, and 6 hrs and culture media collected for cytokine analysis. At 6 hrs (FIG. 41), the results indicated significant time-dependent increase in early inflammatory response in cytokines IL-6 and IL-1β (EIA assay, Cayman chemicals) by LPS, with significantly smaller increases observed with milk exosomes, particularly for IL-6, despite relatively high doses (the levels at 1 and 3 hrs were still lower).

Figure 42:
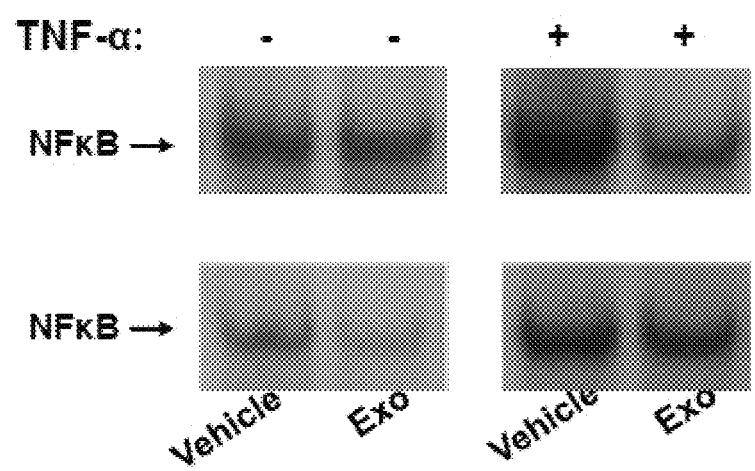
FIG. 42 includes images showing the anti-inflammatory activity of bovine milk-derived exosomes per se, where the inhibition of the constitutive and TNF-α (10 ng/ml)-induced NF-κB in human lung cancer H1299 (A) and A549 (B) cells by milk exosomes (100 μg/ml) was measured by EMSA.
Figure 43:
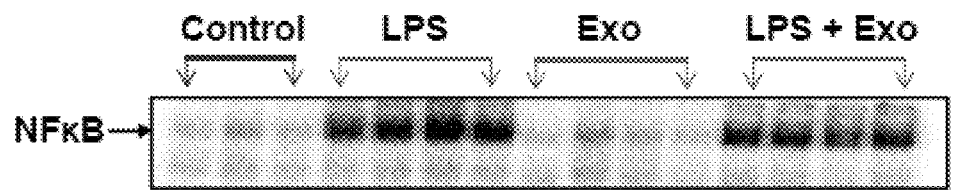
FIG. 43 includes an image showing the anti-inflammatory activity of bovine milk-derived exosomes per se in the lung tissue of Sprague Dawley rats treated with lipopolysaccharide (LPS) as measured by EMSA, where Sprague Dawley rats were treated with LPS (10 mg/kg) and milk exosomes (5 mg Exo protein/rat), both intraperitoneally, alone or in combination for 6 hrs.

Anti-inflammatory activity of bovine milk-derived exosomes per se was also assessed in human lung H1299 and A549 cells, and it was observed that the exosomes were capable of inhibiting constitutive and TNF-α induced NF-κB activation in those cells (FIG. 42). Milk-derived exosomes also showed modest (30-40%) protection against lipopolysaccharide (LPS)-induced NF-κB in the lung of S/D rats (FIG. 43). Similar protective observations were made in liver and brain samples. In the absence of LPS treatment, milk exosomes showed no detectable increase in NF-κB in the lung compared with vehicle treatment, indicating milk exosomes were well tolerated.

Figure 44:
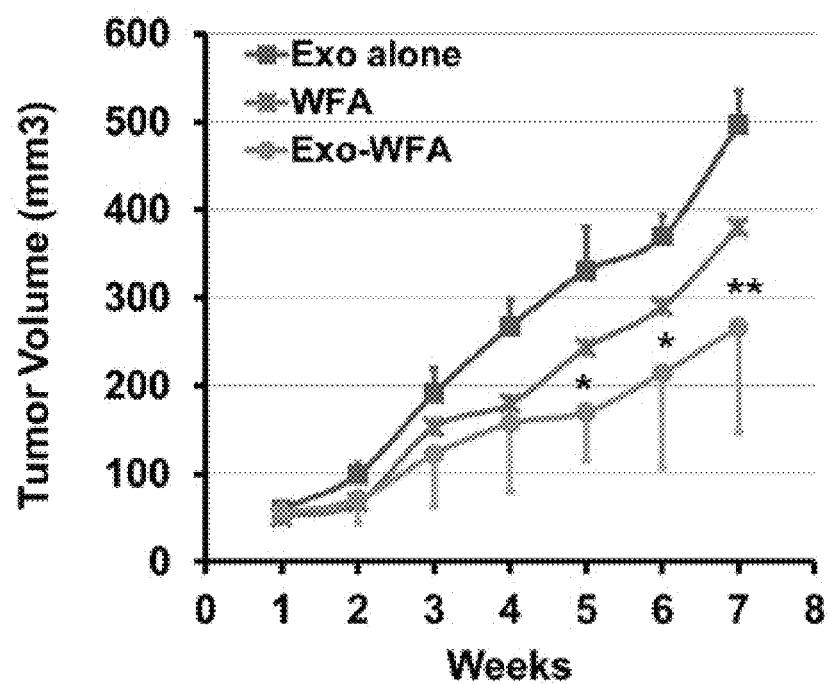
FIG. 44 is a graph showing the antitumor activity of withaferin A (WFA)-loaded milk-derived exosomes, where following inoculation with human lung cancer A549 cells ($3 \times 10^6$ cells), when tumor xenografts grew to over 60 mm$^3$, animals were treated intraperitoneally three times a week with WFA-loaded exosomes (4 mg/kg WFA and 1.3 mg Exo protein/mouse) while two other groups were treated intraperitoneally with exosomes alone (1.3 mg/mouse) or WFA (4 mg/kg)
Figure 45:
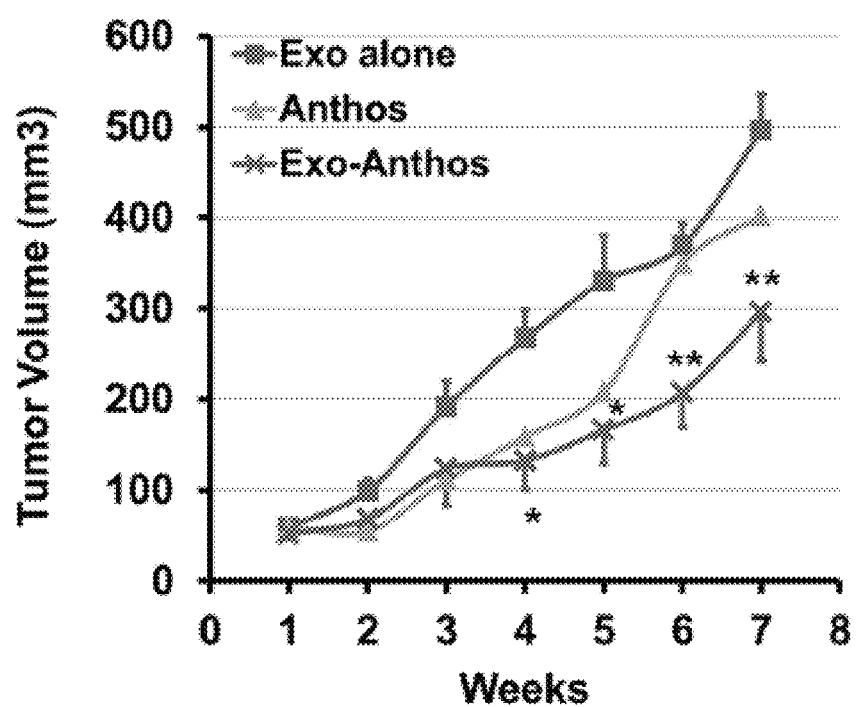
FIG. 45 is a graph showing the anti-tumor activity of milk-derived exosomes loaded with bilberry anthocyanidins, where following inoculation with human lung cancer A549 cells ($3 \times 10^6$ cells), when tumor xenografts grew to over 60 mm$^3$, nude mice were treated intraperitoneally three times a week with anthocyanidins-loaded exosomes (0.25 mg anthocyanidins and 1.3 mg Exo protein per mouse) while two other groups were treated intraperitoneally with exosomes alone (1.3 mg/mouse) or anthocyanidins (0.25 mg/mouse).

Example 11—Anti-Tumor Activity of Therapeutic Agent-Loaded Milk-Derived Exosomes To assess the anti-tumor activity of therapeutic agent-loaded milk-derived exosomes, nude mice were inoculated with human lung A549 cancer cells ($3 \times 10^6$ cells). Following inoculation with the human lung A549 cancer cells, when tumor xenografts grew to over 60 mm³, animals were treated intraperitoneally three times a week with withaferin A-loaded milk exosomes (Exo-WFA, 4 mg/kg WFA and 1.3 mg Exo protein/mouse). Two other groups were treated intraperitoneally with the exosomes alone (1.3 mg/mouse) or with withaferin A (4 mg/kg). Upon analysis of the results, it was observed that exosomally-administered withaferin A significantly reduced tumor volume when compared to the groups administered exosomes alone or withaferin A alone (FIG. 44). Similar experiments were conducted to assess the anti-tumor activity of milk exosomes loaded with bilberry anthocyanidins in human lung A549 cancer cells and it was observed that that exosomally-administered bilberry anthocyanidins also significantly reduced tumor volume when compared to the groups administered exosomes alone or bilberry anthocyanidins alone (FIG. 45).

Discussion of Examples 1-11

The results of the studies described herein above showed that i) bulk exosomes can be isolated from both bovine milk and colostrum; ii) the exosomes generally range from 30-100 nm and yield greater than 300 mg exosomal protein per 100 ml milk; iii) milk and colostrum exosomes can be loaded with a variety of hydrophilic and lipophilic compounds, including chemotherapeutic agents; iv) therapeutic agents embedded in exosomes showed higher anti-proliferative, anti-tumor, and anti-inflammatory activities than free therapeutic agents; and v) exosomes per se (in the absence of therapeutic agent) from both milk and colostrum showed significant cancer cell killing activity.

Throughout this document, various references are mentioned. All such references are incorporated herein by reference, including the references set forth in the following list:

REFERENCES

1. Dolle, J. M., Daling, J. R., White, E., Brinton, L. A., Doody, D. R., Porter, P. L. and Malone, K. E. (2009). Risk factors for triple-negative breast cancer in women under the age of 45 years. Cancer Epidemiol Biomarkers Prev 18, 1157-66.
2. Onitilo, A. A., Engel, J. M., Greenlee, R. T. and Mukesh, B. N. (2009). Breast cancer subtypes based on ER/PR and Her2 expression: comparison of clinicopathologic features and survival. Clin Med Res 7, 4-13.
3. Escudier, B. et al. (2005). Vaccination of metastatic melanoma patients with autologous dendritic cell (DC) derived-exosomes: results of the first phase I clinical trial. J Transl Med 3, 10.
4. Morse, M. A. et al. (2005). A phase I study of dexosome immunotherapy in patients with advanced non-small cell lung cancer. J Transl Med 3, 9.
5. Sun, D. M. et al. (2010). A Novel Nanoparticle Drug Delivery System: The Anti-inflammatory Activity of Curcumin Is Enhanced When Encapsulated in Exosomes. Molecular Therapy 18, 1606-1614.
6. Matsumoto, G., Namekawa, J., Muta, M., Nakamura, T., Bando, H., Tohyama, K., Toi, M. and Umezawa, K. (2005). Targeting of nuclear factor kappa B pathways by dehydroxymethylepoxyquinomicin, a novel inhibitor of breast carcinomas: Antitumor and antiangiogenic potential in vivo. Clinical Cancer Research 11, 1287-1293.
7. Sunters, A. et al. (2003). FoxO3a transcriptional regulation of bim controls apoptosis in paclitaxel-treated breast cancer cell lines. Journal of Biological Chemistry 278, 49795-49805.
8. Downs-Holmes, C. and Silverman, P. (2011). Breast cancer: overview & updates. Nurse Pract 36, 20-6; quiz 7.
9. Dunnwald, L. K., Rossing, M. A. and Li, C. I. (2007). Hormone receptor status, tumor characteristics, and prognosis: a prospective cohort of breast cancer patients. Breast Cancer Res 9, R6.
10. Kausar, H., Jeyabalan, J., Aqil, F., Chabba, D., Sidana, J., Singh, I. P. and Gupta, R. C. (2012). Berry anthocyanidins synergistically suppress growth and invasive potential of human non-small-cell lung cancer cells. Cancer Lett 325, 54-62.
11. Kuo, M. T. (2007). Roles of multidrug resistance genes in breast cancer chemoresistance. Adv Exp Med Biol 608, 23-30.
12. Siegel, R., Ward, E., Brawley, O. and Jemal, A. (2011). Cancer statistics, 2011: the impact of eliminating socioeconomic and racial disparities on premature cancer deaths. CA Cancer J Clin 61, 212-36.
13. Desantis, C., Ma, J., Bryan, L. and Jemal, A. (2013). Breast cancer statistics, 2013. CA Cancer J Clin
14. American_Cancer_Society. Breast Cancer Facts & FIGS. 2011-2012. In American Cancer Society, Inc. ed.). American Cancer Society, Atlanta.
15. Munagala, R., Aqil, F. and Gupta, R. C. (2011). Promising molecular targeted therapies in breast cancer. Indian J Pharmacol 43, 236-45.
16. Xiao, H., Verdier-Pinard, P., Fernandez-Fuentes, N., Burd, B., Angeletti, R., Fiser, A., Horwitz, S. B. and Orr, G. A. (2006). Insights into the mechanism of microtubule stabilization by Taxol. Proc Natl Acad Sci USA 103, 10166-73.
17. Chun, E. and Lee, K. Y. (2004). Bcl-2 and Bcl-xL are important for the induction of paclitaxel resistance in human hepatocellular carcinoma cells. Biochem Biophys Res Commun 315, 771-9.
18. David, O., Jett, J., LeBeau, H., Dy, G., Hughes, J., Friedman, M. and Brody, A. R. (2004). Phospho-Akt overexpression in non-small cell lung cancer confers significant stage-independent survival disadvantage. Clinical Cancer Research 10, 6865-71.
19. Dong, Q. G. et al. (2002). The function of multiple IkappaB:NF-kappaB complexes in the resistance of cancer cells to Taxol-induced apoptosis. Oncogene 21, 6510-9.
20. Yabuki, N., Sakata, K., Yamasaki, T., Terashima, H., Mio, T., Miyazaki, Y., Fujii, T. and Kitada, K. (2007). Gene amplification and expression in lung cancer cells with acquired paclitaxel resistance. Cancer Genet Cytogenet 173, 1-9.
21. Monzo, M. et al. (1999). Paclitaxel resistance in non-small-cell lung cancer associated with beta-tubulin gene mutations. J Clin Oncol 17, 1786-93.
22. Ciardiello, F., Caputo, R., Borriello, G., Del Bufalo, D., Biroccio, A., Zupi, G., Bianco, A. R. and Tortora, G. (2002). ZD1839 (IRESSA), an EGFR-selective tyrosine kinase inhibitor, enhances taxane activity in bcl-2 overexpressing, multidrug-resistant MCF-7 ADR human breast cancer cells. Int J Cancer 98, 463-9.
23. Duan, Z. et al. (2006). Signal transducers and activators of transcription 3 pathway activation in drug-resistant ovarian cancer. Clinical Cancer Research 12, 5055-63.
24. Mine, T. et al. (2009). Breast cancer cells expressing stem cell markers CD44+ CD24 lo are eliminated by Numb-1 peptide-activated T cells. Cancer Immunol Immunother 58, 1185-94.
25. Wu, C. P., Ohnuma, S. and Ambudkar, S. V. (2011). Discovering natural product modulators to overcome multidrug resistance in cancer chemotherapy. Curr Pharm Biotechnol 12, 609-20.
26. Sun, L. R., Cui, S. X. and Qu, X. J. (2009). Overcoming Multidrug Resistance in Cancer: An Update on Research of Natural Products. Drugs of the Future 34, 53-59.
27. Nabekura, T., Kamiyama, S. and Kitagawa, S. (2005). Effects of dietary chemopreventive phytochemicals on P-glycoprotein function. Biochem Biophys Res Commun 327, 866-70.
28. Kannaiyan, R. et al. (2011). Celastrol inhibits proliferation and induces chemosensitization through down-regulation of NF-kappa B and STAT3 regulated gene products in multiple myeloma cells. British Journal of Pharmacology 164, 1506-1521.
29. Aisner, J. (2007). Overview of the changing paradigm in cancer treatment: oral chemotherapy. Am J Health Syst Pharm 64, S4-7.
30. Joo, K. M., Park, K., Kong, D. S., Song, S. Y., Kim, M. H., Lee, G. S., Kim, M. S. and Nam, D. H. (2008). Oral paclitaxel chemotherapy for brain tumors: ideal combination treatment of paclitaxel and P-glycoprotein inhibitor. Oncol Rep 19, 17-23.
31. Yang, F., Jin, C., Jiang, Y., Li, J., Di, Y., Ni, Q. and Fu, D. (2011). Liposome based delivery systems in pancreatic cancer treatment: from bench to bedside. Cancer Treat Rev 37, 633-42.
32. Bansal, S. S., Kausar, H., Aqil, F., Jeyabalan, J., Vadhanam, M. V., Gupta, R. C. and Ravoori, S. (2011). Curcumin implants for continuous systemic delivery: safety and biocompatibility. Drug Deliv. and Transl. Res. 1, 332-341.
33. Feng, L. and Mumper, R. J. (2013). A critical review of lipid-based nanoparticles for taxane delivery. Cancer Lett 334, 157-75.
34. Kooijmans, S. A., Vader, P., van Dommelen, S. M., van Solinge, W. W. and Schiffelers, R. M. (2012). Exosome mimetics: a novel class of drug delivery systems. Int J Nanomedicine 7, 1525-41.
35. Lakhal, S. and Wood, M. J. (2011). Exosome nanotechnology: an emerging paradigm shift in drug delivery: exploitation of exosome nanovesicles for systemic in vivo delivery of RNAi heralds new horizons for drug delivery across biological barriers. Bioessays 33, 737-41.
36. Aiyer, H. S., Srinivasan, C. and Gupta, R. C. (2008). Dietary berries and ellagic acid diminish estrogen-mediated mammary tumorigenesis in ACI rats. Nutr Cancer 60, 227-34.
37. Ravoori, S., Vadhanam, M. V., Aqil, F. and Gupta, R. C. (2012). Inhibition of estrogen-mediated mammary tumorigenesis by blueberry and black raspberry. J Agric Food Chem 60, 5547-55.
38. Gupta, R. C. et al. (2012). Controlled-release systemic delivery—a new concept in cancer chemoprevention. Carcinogenesis 33, 1608-15.
39. Chou, T. C. and Talalay, P. (1984). Quantitative analysis of dose-effect relationships: the combined effects of multiple drugs or enzyme inhibitors. Adv Enzyme Regul 22, 27-55.
40. Stan, S. D., Hahm, E. R., Warin, R. and Singh, S. V. (2008). Withaferin A causes FOXO3a- and Bim-dependent apoptosis and inhibits growth of human breast cancer cells in vivo. Cancer Res 68, 7661-9.
41. Das, K. C. and White, C. W. (1997). Activation of NF-kappa B by antineoplastic agents—Role of protein kinase C. Journal of Biological Chemistry 272, 14914-14920.
42. Aggarwal, B. B., Shishodia, S., Takada, Y., Banerjee, S., Newman, R. A., Bueso-Ramos, C. E. and Price, J. E. (2005). Curcumin suppresses the paclitaxel-induced nuclear factor-kappa B pathway in breast cancer cells and inhibits lung metastasis of human breast cancer in nude mice. Clinical Cancer Research 11, 7490-7498.
43. Kaileh, M. et al. (2007). Withaferin a strongly elicits IkappaB kinase beta hyperphosphorylation concomitant with potent inhibition of its kinase activity. Journal of Biological Chemistry 282, 4253-64.
44. Sun, D., Zhuang, X., Zhang, S., Deng, Z. B., Grizzle, W., Miller, D. and Zhang, H. G. (2013). Exosomes are endogenous nanoparticles that can deliver biological information between cells. Adv Drug Deliv Rev 65, 342-7.
45. Gill, K. K., Kaddoumi, A. and Nazzal, S. (2012). Mixed micelles of PEG(2000)-DSPE and vitamin-E TPGS for concurrent delivery of paclitaxel and parthenolide: enhanced chemosenstization and antitumor efficacy against non-small cell lung cancer (NSCLC) cell lines. Eur J Pharm Sci 46, 64-71.
46. Hogue, M., Dave, S., Gupta, P. and Saleemuddin, M. (2013). Oleic Acid May Be the Key Contributor in the BAMLET-Induced Erythrocyte Hemolysis and Tumoricidal Action. PLoS One 8, e68390.
47. Liskova, K., Kelly, A. L., O'Brien, N. and Brodkorb, A. (2010). Effect of denaturation of alpha-lactalbumin on the formation of BAMLET (bovine alpha-lactalbumin made lethal to tumor cells). J Agric Food Chem 58, 4421-7.
48. Rammer, P. et al. (2010). BAMLET activates a lysosomal cell death program in cancer cells. Molecular Cancer Therapeutics 9, 24-32.
49. Jenkins, D. E., Hornig, Y. S., Oei, Y., Dusich, J. and Purchio, T. (2005). Bioluminescent human breast cancer cell lines that permit rapid and sensitive in vivo detection of mammary tumors and multiple metastases in immune deficient mice. Breast Cancer Research 7, R444-R454.

50. Stan, S. D., Zeng, Y. and Singh, S. V. (2008). Ayurvedic medicine constituent withaferin a causes G2 and M phase cell cycle arrest in human breast cancer cells. Nutr Cancer 60 Suppl 1, 51-60.
51. Munagala, R., Kausar, H., Munjal, C. and Gupta, R. C. (2011). Withaferin A induces p53-dependent apoptosis by repression of HPV oncogenes and upregulation of tumor suppressor proteins in human cervical cancer cells. Carcinogenesis 32, 1697-705.
52. Srinivasan, S., Ranga, R. S., Burikhanov, R., Han, S. S. and Chendil, D. (2007). Par-4-dependent apoptosis by the dietary compound withaferin A in prostate cancer cells. Cancer Res 67, 246-53.
53. Aqil, F., Jeyabalan, J., Kausar, H., Bansal, S. S., Sharma, R. J., Singh, I. P., Vadhanam, M. V. and Gupta, R. C. (2012). Multi-layer polymeric implants for sustained release of chemopreventives. Cancer Lett 326, 33-40.
54. Yu, Y. et al. (2010). Withaferin A targets heat shock protein 90 in pancreatic cancer cells. Biochem Pharmacol 79, 542-51.
55. Maitra, R., Porter, M. A., Huang, S. and Gilmour, B. P. (2009). Inhibition of NFkappaB by the natural product Withaferin A in cellular models of Cystic Fibrosis inflammation. J Inflamm (Lond) 6, 15.
56. Killion, J. J., Radinsky, R. and Fidler, I. J. (1998). Orthotopic models are necessary to predict therapy of transplantable tumors in mice. Cancer Metastasis Rev 17, 279-84.
57. Nakayama, S. et al. (2009). Prediction of paclitaxel sensitivity by CDK1 and CDK2 activity in human breast cancer cells. Breast Cancer Res 11, R12.
58. Jenkins, D. E., Oei, Y., Hornig, Y. S., Yu, S. F., Dusich, J., Purchio, T. and Contag, P. R. (2003). Bioluminescent imaging (BLI) to improve and refine traditional murine models of tumor growth and metastasis. Clin Exp Metastasis 20, 733-744.
59. Richert, M. M. et al. (2005). Metastasis of hormone-independent breast cancer to lung and bone is decreased by alpha-difluoromethylornithine treatment. Breast Cancer Res 7, R819-27.
60. Dadiani, M., Kalchenko, V., Yosepovich, A., Margalit, R., Hassid, Y., Degani, H. and Seger, D. (2006). Real-time imaging of lymphogenic metastasis in orthotopic human breast cancer. Cancer Res 66, 8037-41.
61. Cleator, S., Heller, W. and Coombes, R. C. (2007). Triple-negative breast cancer: therapeutic options. Lancet Oncol 8, 235-44.
62. Gluz, O., Liedtke, C., Gottschalk, N., Pusztai, L., Nitz, U. and Harbeck, N. (2009). Triple-negative breast cancer—current status and future directions. Ann Oncol 20, 1913-27.
63. Kutuk, O. and Letai, A. (2008). Alteration of the mitochondrial apoptotic pathway is key to acquired paclitaxel resistance and can be reversed by ABT-737. Cancer Research 68, 7985-7994.
64. Weigelt, B., Peterse, J. L. and van't Veer, L. J. (2005). Breast cancer metastasis: markers and models. Nat Rev Cancer 5, 591-602.
65. Nakshatri, H., Bhat-Nakshatri, P., Martin, D. A., Goulet, R. J., Jr. and Sledge, G. W., Jr. (1997). Constitutive activation of NF-kappaB during progression of breast cancer to hormone-independent growth. Mol Cell Biol 17, 3629-39.
66. Huber, M. A. et al. (2004). NF-kappaB is essential for epithelial-mesenchymal transition and metastasis in a model of breast cancer progression. J Clin Invest 114, 569-81.
67. Das, K. C. and White, C. W. (1997). Activation of NF-kappaB by antineoplastic agents. Role of protein kinase C. Journal of Biological Chemistry 272, 14914-20.
68. Aggarwal, B. B., Shishodia, S., Takada, Y., Banerjee, S., Newman, R. A., Bueso-Ramos, C. E. and Price, J. E. (2005). Curcumin suppresses the paclitaxel-induced nuclear factor-kappaB pathway in breast cancer cells and inhibits lung metastasis of human breast cancer in nude mice. Clin Cancer Res 11, 7490-8.
69. Kang, H. J., Lee, S. H., Price, J. E. and Kim, L. S. (2009). Curcumin suppresses the paclitaxel-induced nuclear factor-kappaB in breast cancer cells and potentiates the growth inhibitory effect of paclitaxel in a breast cancer nude mice model. Breast J 15, 223-9.
70. Wang, L., Brugge, J. S. and Janes, K. A. (2011). Intersection of FOXO- and RUNX1-mediated gene expression programs in single breast epithelial cells during morphogenesis and tumor progression. Proc Natl Acad Sci USA 108, E803-12.
71. Zhang, Y. Q., Gan, B. Y., Liu, D. and Paik, J. H. (2011). FoxO family members in cancer. Cancer Biology & Therapy 12, 253-259.
72. Chovolou, Y., Lupertz, R., Pavkovic, M., Kahl, R. and Watjen, W. (2011). Molecular Effects of FOXO in Human Cancer Cells. Naunyn-Schmiedebergs Archives of Pharmacology 383, 3-3.
73. Scalera, F., Dittrich, R., Beckmann, M. W. and Beinder, E. (2002). Effect of endothelin-1 on intracellular glutathione and lipid peroxide availability and on the secretion of vasoactive substances by human umbilical vein endothelial cells. Eur J Clin Invest 32, 556-62.
74. Kim, J. S., He, L. and Lemasters, J. J. (2003). Mitochondrial permeability transition: a common pathway to necrosis and apoptosis. Biochem Biophys Res Commun 304, 463-70.
75. Kroemer, G., Galluzzi, L. and Brenner, C. (2007). Mitochondrial membrane permeabilization in cell death. Physiol Rev 87, 99-163.
76. Rahn, C. A., Bombick, D. W. and Doolittle, D. J. (1991). Assessment of mitochondrial membrane potential as an indicator of cytotoxicity. Fundam Appl Toxicol 16, 435-48.
77. Ferreira, C. G., Span, S. W., Peters, G. J., Kruyt, F. A. and Giaccone, G. (2000). Chemotherapy triggers apoptosis in a caspase-8-dependent and mitochondria-controlled manner in the non-small cell lung cancer cell line NCI-H460. Cancer Res 60, 7133-41.
78. Yan, F. et al. (2012). Gambogenic acid induced mitochondrial-dependent apoptosis and referred to Phospho-Erk1/2 and Phospho-p38 MAPK in human hepatoma HepG2 cells. Environ Toxicol Pharmacol 33, 181-90.
79. Han, L. L., Xie, L. P., Li, L. H., Zhang, X. W., Zhang, R. Q. and Wang, H. Z. (2009). Reactive oxygen species production and Bax/Bcl-2 regulation in honokiol-induced apoptosis in human hepatocellular carcinoma SMMC-7721 cells. Environ Toxicol Pharmacol 28, 97-103.
80. Pazos, P., Lanari, C., Meiss, R., Charreau, E. H. and Pasqualini, C. D. (1992). Mammary carcinogenesis induced by N-methyl-N-nitrosourea (MNU) and medroxyprogesterone acetate (MPA) in BALB/c mice. Breast Cancer Res Treat 20, 133-8.
81. Bansal, S. S., Kausar, H., Vadhanam, M. V., Ravoori, S. and Gupta, R. C. (2011). Controlled systemic delivery by polymeric implants enhances tissue and plasma curcumin levels compared with oral administration. European Journal of Pharmaceutics and Biopharmaceutics 82. Cao, P. X., Vadhanam, M. V., Spencer, W. A., Cai, J. and Gupta, R. C. (2011). Sustained Systemic Delivery of Green Tea Polyphenols by Polymeric Implants Significantly Diminishes Benzo[a]pyrene-Induced DNA Adducts. Chemical Research in Toxicology 24, 877-886.
83. Bansal, S. S., Vadhanam, M. V. and Gupta, R. C. (2011). Development and In Vitro-In Vivo Evaluation of Polymeric Implants for Continuous Systemic Delivery of Curcumin. Pharmaceutical Research 28, 1121-1130.
84. Thaiparambil, J. T. et al. (2011). Withaferin A inhibits breast cancer invasion and metastasis at sub-cytotoxic doses by inducing vimentin disassembly and serine 56 phosphorylation. International Journal of Cancer 129, 2744-2755.
85. Huizing, M. T. et al. (1993). Pharmacokinetics of paclitaxel and metabolites in a randomized comparative study in platinum-pretreated ovarian cancer patients. Journal of Clinical Oncology 11, 2127-35.
86. Huizing, M. T., Sparreboom, A., Rosing, H., van Tellingen, O., Pinedo, H. M. and Beijnen, J. H. (1995). Quantification of paclitaxel metabolites in human plasma by high-performance liquid chromatography. J Chromatogr B Biomed Appl 674, 261-8.
87. Cao, P., Cai, J. and Gupta, R. C. (2010). Effect of green tea catechins and hydrolyzable tannins on benzo[a]pyrene-induced DNA adducts and structure-activity relationship. Chem Res Toxicol 23, 771-7.
88. Aqil, F., Munagala, R., Vadhanam, M. V., Kausar, H., Jeyabalan, J., Schultz, D. J. and Gupta, R. C. (2012). Anti-proliferative activity and protection against oxidative DNA damage by punicalagin isolated from pomegranate husk. Food Res Int 49, 345-353.
89. Hemminki, K (2003) DNA adducts, mutations, and cancer. Carcinogenesis, 14, 2007-12.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition, comprising an effective amount of a therapeutic agent encapsulated by a milk-derived microvesicle, wherein the therapeutic agent is a chemotherapeutic agent selected from, taxane compounds, anti-tumor *vinca* alkaloids, anti-tumor anthracycline derivatives, HER2 antibodies, DNA methyl transferase inhibitors, actinomycin D, adriamycin, capecitabine, carboplatin, cisplatin, daunorubicin, doxorubicin, 5-fluorouracil, gemcitabine, idarubicin, mitoxantrone, oxaliplatin, retinoids, retinoic acid metabolism blocking agents (RAMBA), taxol, vinblastine, vincristine, vinorelbine, vitamin D, Accutane, and combinations thereof.

2. The composition of claim 1 wherein the chemotherapeutic agent is a taxane compound selected from paclitaxel, docetaxel or combinations thereof.
3. The composition of claim 1 wherein the chemotherapeutic agent is a HER2 antibody selected from trastuzumab, estrogen receptor antagonists, or combinations thereof.
4. The composition of claim 1 wherein the chemotherapeutic agent is a DNA methyl transferase inhibitor selected from azacytidine.
5. The composition of claim 1 wherein the chemotherapeutic agent is a retinoic acid, 5-fluorouracil, vincristine, actinomycin D, adriamycin, cisplatin, docetaxel, doxorubicin, taxol, paclitaxel or a combination thereof.
6. The composition of claim 5 wherein the chemotherapeutic agent is doxorubicin.
7. The composition of claim 5 wherein the chemotherapeutic agent is paclitaxel.
8. The composition of claim 5 wherein the chemotherapeutic agent is docetaxel.
9. The composition of claim 1 wherein the therapeutic agent loading is from 3.8% to 65%.
10. The composition of claim 1 wherein the milk-derived microvesicle is a colostrum-derived microvesicle.
11. The composition of claim 1 further comprising one or more miRNA or siRNA molecules in the milk-derived microvesicle.
12. The composition of claim 11 wherein the one or more miRNA molecules are selected from the group consisting of miR-155 and miR-223.
13. The composition of claim 1 further comprising a pharmaceutically-acceptable vehicle, carrier, or excipient.
14. A composition, comprising a therapeutic agent encapsulated by a milk-derived microvesicle, wherein the milk-derived microvesicle is isolated by obtaining an amount of milk and subjecting the milk to a first centrifugation at 20,000×g at 4° C. for 30 min, and then a second centrifugation at 100,000×g at 4° C. for 60 min, and then a third centrifugation at 120,000×g at 4° C. for 90 min, such that a yield greater than about 50 mg of microvesicle protein per 100 ml of milk is recovered, and wherein the therapeutic agent is a chemotherapeutic agent selected from doxorubicin, paclitaxel, docetaxel, and combinations thereof.
15. The composition of claim 14 wherein the milk is raw milk or colostrum.
16. The composition of claim 14 wherein the therapeutic agent loading is from 3.8% to 65%.
17. The composition of claim 1 wherein the milk-derived microvesicle is derived from raw milk or colostrum.
18. The composition of claim 17 wherein the raw milk is bovine raw milk.
19. The composition of claim 17 wherein the colostrum is bovine colostrum.

* * * * *